(12) United States Patent
Gawlitzek et al.

(10) Patent No.: US 8,512,983 B2
(45) Date of Patent: Aug. 20, 2013

(54) PRODUCTION OF PROTEINS IN GLUTAMINE-FREE CELL CULTURE MEDIA

(76) Inventors: Martin Gawlitzek, Redwood City, CA (US); Shun Luo, Irvine, CA (US); Christina Teresa Petraglia, San Ramon, CA (US)

(*) Notice: Subject to any disclaimer, the term of this patent is extended or adjusted under 35 U.S.C. 154(b) by 151 days.

(21) Appl. No.: 12/852,377

(22) Filed: Aug. 6, 2010

(65) Prior Publication Data

US 2011/0091936 A1 Apr. 21, 2011

Related U.S. Application Data

(60) Provisional application No. 61/232,889, filed on Aug. 11, 2009.

(51) Int. Cl.
C12P 21/06 (2006.01)

(52) U.S. Cl.
USPC ........................................................ 435/69.1

(58) Field of Classification Search
USPC ........................................................ 435/69.1
See application file for complete search history.

(56) References Cited

U.S. PATENT DOCUMENTS

| | | |
|---|---|---|
| 4,049,494 A * | 9/1977 | Tomei ............................. 435/239 |
| 4,399,216 A | 8/1983 | Axel et al. |
| 4,515,893 A | 5/1985 | Kung et al. |
| 4,560,655 A | 12/1985 | Baker |
| 4,657,866 A | 4/1987 | Kumar |
| 4,766,075 A | 8/1988 | Goeddel et al. |
| 4,767,704 A | 8/1988 | Cleveland et al. |
| 4,816,567 A | 3/1989 | Cabilly et al. |
| 4,853,330 A | 8/1989 | Goeddel et al. |
| 4,927,762 A | 5/1990 | Darfler |
| 5,091,313 A | 2/1992 | Chang |
| 5,122,469 A | 6/1992 | Mather et al. |
| 5,185,259 A | 2/1993 | Goeddel et al. |
| 5,500,362 A | 3/1996 | Robinson et al. |
| 5,545,806 A | 8/1996 | Lonberg et al. |
| 5,545,807 A | 8/1996 | Surani et al. |
| 5,569,825 A | 10/1996 | Lonberg et al. |
| 5,622,700 A | 4/1997 | Jardieu et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,672,347 A | 9/1997 | Aggarwal et al. |
| 5,693,762 A | 12/1997 | Queen et al. |
| 5,714,338 A | 2/1998 | Wai Fei et al. |
| 5,721,108 A | 2/1998 | Robinson et al. |
| 5,725,856 A | 3/1998 | Hudziak et al. |
| 5,736,137 A | 4/1998 | Anderson et al. |
| 5,750,373 A | 5/1998 | Garrard et al. |
| 5,776,456 A | 7/1998 | Anderson et al. |
| 5,821,333 A | 10/1998 | Carter et al. |
| 5,821,337 A | 10/1998 | Carter et al. |
| 5,843,439 A | 12/1998 | Anderson et al. |
| 6,075,181 A | 6/2000 | Kucherlapati et al. |
| 6,150,584 A | 11/2000 | Kucherlapati et al. |
| 6,171,586 B1 | 1/2001 | Lam et al. |
| 6,194,551 B1 | 2/2001 | Idusogie et al. |
| 6,242,195 B1 | 6/2001 | Idusogie et al. |
| 6,399,061 B1 | 6/2002 | Anderson et al. |
| 6,455,043 B1 | 9/2002 | Grillo-Lopez |
| 6,528,624 B1 | 3/2003 | Idusogie et al. |
| 6,538,124 B1 | 3/2003 | Idusogie et al. |
| 6,610,516 B1 | 8/2003 | Anderson et al. |
| 6,982,321 B2 | 1/2006 | Winter |
| 7,060,269 B1 | 6/2006 | Baca et al. |
| 7,087,409 B2 | 8/2006 | Barbas, III et al. |
| 7,169,901 B2 | 1/2007 | Baca et al. |
| 7,297,334 B2 | 11/2007 | Baca et al. |
| 2002/0004587 A1 | 1/2002 | Miller et al. |
| 2002/0006404 A1 | 1/2002 | Hanna |
| 2002/0009444 A1 | 1/2002 | Grillo-Lopez |
| 2002/0012665 A1 | 1/2002 | Hanna |
| 2002/0058029 A1 | 5/2002 | Hanna |
| 2002/0128488 A1 | 9/2002 | Yamakawa et al. |
| 2002/0197255 A1 | 12/2002 | Anderson et al. |
| 2002/0197256 A1 | 12/2002 | Grewal |
| 2003/0021781 A1 | 1/2003 | Anderson et al. |
| 2003/0082172 A1 | 5/2003 | Anderson et al. |
| 2003/0095963 A1 | 5/2003 | Anderson et al. |
| 2003/0103971 A1 | 6/2003 | Hariharan et al. |
| 2003/0147885 A1 | 8/2003 | Anderson et al. |

(Continued)

FOREIGN PATENT DOCUMENTS

| | | |
|---|---|---|
| EP | 0117058 | 8/1990 |
| EP | 0117059 | 12/1991 |

(Continued)

OTHER PUBLICATIONS

Nagle et al. 1971; An improved heat-stable glutamine-free chemically defined medium for growth of mammalian cells. J. Cell Physiol. 77: 259-264.*

(Continued)

*Primary Examiner* — Karen Cochrane Carlson
(74) *Attorney, Agent, or Firm* — Connie Wong; Christopher De Vry; Arnold & Porter LLP

(57) ABSTRACT

The present invention relates generally to glutamine-free cell culture media supplemented with asparagine. The invention further concerns the production of recombinant proteins, such as antibodies, in asparagine-supplemented glutamine-free mammalian cell culture.

25 Claims, 25 Drawing Sheets

(56) References Cited

U.S. PATENT DOCUMENTS

| | | | |
|---|---|---|---|
| 2004/0186051 | A1 | 9/2004 | Kelley et al. |
| 2005/0070689 | A1* | 3/2005 | Dixit et al. ............... 530/350 |
| 2006/0246004 | A1 | 11/2006 | Adams et al. |

FOREIGN PATENT DOCUMENTS

| | | |
|---|---|---|
| EP | 0307247 | 8/1995 |
| EP | 0404097 | 8/1997 |
| EP | 0117060 | 8/2007 |
| EP | 0420937 | 9/2008 |
| EP | 2464725 | 11/2012 |
| WO | WO 87/00195 | 1/1987 |
| WO | WO 89/05859 | 6/1989 |
| WO | WO 90/03430 | 4/1990 |
| WO | WO 91/00358 | 1/1991 |
| WO | WO 91/10741 | 7/1991 |
| WO | WO 93/04173 | 3/1993 |
| WO | WO 93/11161 | 6/1993 |
| WO | WO 95/19181 | 7/1995 |
| WO | WO 95/23865 | 9/1995 |
| WO | WO 96/30046 | 10/1996 |
| WO | WO 96/33735 | 10/1996 |
| WO | WO 96/34096 | 10/1996 |
| WO | WO 96/40210 | 12/1996 |
| WO | WO 97/25428 | 7/1997 |
| WO | WO 97/26912 | 7/1997 |
| WO | WO 98/06248 | 2/1998 |
| WO | WO 98/23761 | 6/1998 |
| WO | WO 98/24893 | 6/1998 |
| WO | WO 98/45331 | 10/1998 |
| WO | WO 98/51793 | 11/1998 |
| WO | WO 98/56418 | 12/1998 |
| WO | WO 98/58964 | 12/1998 |
| WO | WO 99/22764 | 5/1999 |
| WO | WO 99/51642 | 10/1999 |
| WO | WO 00/09160 | 2/2000 |
| WO | WO 00/27428 | 5/2000 |
| WO | WO 00/27433 | 5/2000 |
| WO | WO 00/42072 | 7/2000 |
| WO | WO 00/44788 | 8/2000 |
| WO | WO 00/67796 | 11/2000 |
| WO | WO 00/75348 | 12/2000 |
| WO | WO 01/03734 | 1/2001 |
| WO | WO 01/10460 | 2/2001 |
| WO | WO 01/10461 | 2/2001 |
| WO | WO 01/10462 | 2/2001 |
| WO | WO 01/40309 | 6/2001 |
| WO | WO 01/74388 | 10/2001 |
| WO | WO 01/77342 | 10/2001 |
| WO | WO 01/80884 | 11/2001 |
| WO | WO 01/97858 | 12/2001 |
| WO | WO 02/04021 | 1/2002 |
| WO | WO 02/34790 | 5/2002 |
| WO | WO 02/060955 | 8/2002 |
| WO | WO 02/079255 | 10/2002 |
| WO | WO 02/096948 | 12/2002 |
| WO | WO 2004/092219 | 10/2004 |
| WO | 2006083971 | * 10/2006 |

OTHER PUBLICATIONS

Kurano et al. 1990; Growth behavior of Chinese hamster ovary cells in a compact loop bioreactor. 2. Effects of medium components and waste products. J. Biotechnol. 15: 113-128.* www. products.invitrogen.com/ivgn/product/A1049001; 2012.*

Sanfeliu et al. 1999; Effect of glutamine limitation on the death of attached Chinese hamster ovary cells. Biotechnol. Bioeng. 64: 46-53.* www. sigmaaldrich.com/life-science/cell-culture/learning-center/media-formulations; 2012.*

De la Cruz Edmonds et al. 2006; Development of transfection and high-producer screening protocols for the CHOK1SV cell system. Molecular Biotechnology 34: 179-190.* www. Invitrogen.com/1/1/10163-cd-cho-medium-1x-liquid.html; 2012.*

Wu et al. 2001; Multimerization of chimeric anti-CD20 single-chain Fv-Fc fusion protein is mediated through variable domain exchange. Protein Engineering 14(12): 1025-1033.*

Beck et al. 2008; Trends in glycosylation, glycoanalysis, and glycoengineering of therapeutic antibodies and Fc-Fusion proteins. Current Pharmaceutical Biotechnology 9(6): 482-501.*

Haiyan Huang, et al., "Nitrogen metabolism of asparagine and glutamate in Vero cells studied by 1H/15N NMR spectroscopy", Applied Microbiology and Biotechnology, Springer, Berlin, DE LNKD-DOI: 10.1007/S00253-007-1181-8, vol. 77, No. 2, Oct. 19, 2007, pp. 427-436, XP019560711, ISSN: 1432-0614.

Kurano N., et al., "Growth behavior of Chinese hamster ovary cells in a compact loop biorcactor. 2. Effects of medium components and waste products", Journal of Biotechnology, Elsevier Science Publishers, Amsterdam, NL LNKD-DOI: 10.1016/0168-1656 (90) 90055-G, vol. 15, No. 1-2, Jul. 1, 1990, pp. 113-128, XP023944043, ISSN: 0168-1656, [retrieved on Jul. 1, 1990].

GB 2 237 288 A (Celltech Ltd [GB]), May 1, 1991, Abstract, p. 4, paragraphs 2, 3, 5; claim 8.

Altamirano, et al., "Strategies for fed-batch cultivation of t-PA producing CHO cells: substitution of glucose and glutamine and rational design of culture medium", Journal of Biotechnology, 110: 171-179, (2004).

Miller, et al., "A kinetic analysis of hybridoma growth and metabolism in batch and continuous suspension culture: Effect of nutrient concentration, dilution rate, and pH", Biotechnology and Bioengineering, vol. 32, pp. 947-965, (1988).

Sanfeliu, et al., "Effect of Glutamine limitation on the death of attached Chinese hamster ovary cells", Biotechnology and Bioengineering, 64: pp. 46-53, (1999).

Schneider, et al., "The importance of ammonia in mammalian cell culture", Journal of Biotechnology, 46: 161-185, (1996).

Aruffo et al. "CD44 is the Principal Cell Surface Receptor for Hyaluronate", Cell vol. 61, 1303-1313, 1990.

Barbas et al. "In Vitro Evolution of a Neutralizing Human Antibody to Human Immunodeficiency Virus Type 1 to Enhance Affinity and Broaden Strain Cross-Reactivity", Proc. Natl. Acad. Sci. USA; vol. 91, pp. 3809-3813, 1994.

Barnes and Sato "Methods for Growth of Cultured Cells in Serum-Free Medium", Analytical Biochemistry 102: 255, 1980.

Barnes et al. "Serum-Free Cell Culture: a Unifying Approach", Cell, vol. 22, 649-655,1980.

Baumann et al. "Dexammethasone Regulates the Program of Secretory Glycoprotein Synthesis in Hepatoma Tissue Culture Cells", J. Cell Biology, vol. 85, pp. 1-8, 1980.

Bird et al. "Single-Chain Antigen-Binding proteins", Science vol. 242, pp. 423-426, 1988.

Boerner et al "Production of antigen-specific human monoclonal antibodies from in vitro-primed human splenocytes:", J. of Immunology, vol. 147, No. 1, pp. 86-95, 1991.

Brennan et al. "Preparation of Bispecific Antibodies by Chemical Recombination of Monoclonal Immunoglobulin $G_1$ Fragments", Science 229:81, 1985.

Brodeur et al., Monoclonal Antibody Production Techniques and Applications, pp. 51-63, 1987 (Marcel Dekker, Inc., New York).

Bruggemann et al. "Designer Mice: The Production of Human Antibody Repertoires in Transgenic Animals", Year Immunol. vol. 7, p. 33-40, 1993.

Burton, D.R. "Immunoglobulin G:Functional Sites", Molecular Immunology vol. 22:161-206, 1985.

Capel et al. "Heterogeneity of human IgG Fc receptors", Immunomethods vol. 4, pp. 25-34, 1994.

Carter et al. "High Level *Escherichia coli* Expression and Production of a Bivalent Humanized Antibody Fragment", Biotechnology 10:163-167, 1992.

Clackson et al. "Making antibody fragments using phage display libraries", Nature, vol. 352, pp. 624-628, 1991.

Clynes et al. "Fc receptors are required in passive and active immunity to melanoma", Proc. Natl. Acad. Sci. (USA); vol. 95, pp. 652-656, 1998.

Cole et al. "The EBV-Hybridoma Technique and its application to Human Lung Cancer" Monoclonal Antibodies and Cancer Therapy, pp. 77-96, 1985.

Daeron M. "Fc Receptor Biology", Annu. Rev. Immunol.: 15: 203-34, 1997.
Duchosal et al. "Immunization of hu-PBL-SCID Mice and the Rescue of Human Monoclonal Fab Fragments through Combinatorial Libraries" Nature 355:258, 1992.
Fellouse et al. "Synthetic Antibodies from a Four-Amino-Acid Code: A Dominant role for Tyrosine in Antigen Recognition", PNAS: vol. 101; No. 34: 12467-12472, 2004.
Fishwild et al "High-Avidity Human IgGk Monoclonal Antibodies from a Novel Strain of Minilocus Transgenic Mice", Nature Biotech; vol. 14, pp. 845-851, 1996.
Gasser et al. "Expression of Abbreviated Mouse Dihydrofolate Reductase Genes in Cultured Hamster Cells", Proc. Natl. Acad. Sci. USA vol. 79, pp. 6522-6526, 1982.
Gazzano-Santoro et al. "A Non-Radioactive Complement-Dependent Cytotoxicity Assay for Anti-CD20 Monoclonal Antibody", J of Immunol Methods 202, pp. 163-171, 1997.
Gething et al. "Cell-surface Expression of Influenza Haemagglutinin from a Cloned DNA the RNA Gene", Nature vol. 293: 620-625, 1981.
Ghetie et al. "FcRn: the MHC Class I-Related Receptor that is more than an IgG Transporter" vol. 18, No. 12, pp. 592-598, 1997.
Ghetie et al. "Increasing the Serum Persistence of an IgG Fragment by Random Mutagenesis", Nature Biotech vol. 15, pp. 637-640, 1997.
Goding J.W. "Monoclonal Antibodies: Principles and Practice" pp. 59-103. (Academic Press, 1986).
Graham et al. "Characteristics of a Human Cell Line Transformed by DNA from Human Adenovirus Type 5", J. Gen. Virol:36, 59-72, 1977.
Graham et al. "A New Technique for the Assay of Infectivity of Human Adenovirus 5 DNA" Virology 52, 456-467, 1973.
Gruber et al. "Efficient Tumor Cell Lysis Mediated by a Bispecific Single Chain Antibody Expressed in *Escherichia coli*" J. Immunol. 152:5368, 1994.
Gueffroy, D. "A Guide for the Preparation and Use of buffers in Biological Systems" Cal Biochem Corporation, 1975.
Guyer et al. "Immunoglobulin Binding by Mouse Intestinal Epithelial Cell Receptors" Journal of Immunology; vol. 117, No. 2, pp. 587-593, 1976.
Haas et al. "FcYreceptors of phagocytes", J. Lab. Clin Med 126: 330-41, 1995.
Ham et al. "Media and Growth Requirements" Meth. Enz., 58: 44, 1979.
Hamers-Casterman et al. "Naturally Occurring Antibodies Devoid of Light Chains", Nature vol. 363, pp. 446-448, 1993.
Hammerling et al. "Monoclonal Antibodies and T-Cell Hybridomas", Elsevier; pp. 563-681, 1981.
Harris et al. "Production of Humanized Monoclonal Antibodies for in Vivo Imaging and Therapy", Biochemical Society Transactions; vol. 23, pp. 1035-1038, 1995.
Hawkins et al. "Selection of Phage Antibodies by Binding Affinity Mimicking Affinity Maturation", J. Mol. Biol.; vol. 226, pp. 889-896, 1992.
Hinton et al. "Engineered Human IgG Antibodies with Longer Serum Half-lives in Primates", J. Biol. Chemistry, vol. 279, No. 8, pp. 6213-6216, 2004.
Holliger et al. "Diabodies: Small Bivalent and Bispecific Antibody Fragments" Proc. Natl. Acad. Sci. USA; vol. 90, pp. 6444-6448, 1993.
Hongo et al. Development and Characterization of Murine Monoclonal Antibodies to the Latency-Associated Peptide of Transforming Growth Factor β1 ; Hybridoma; vol. 14, No. 3, pp. 253-260, 1995.
Hoogenboom et al. "By-passing Immunisation Human Antibodies from Synthetic Repertoires of Germline Vh Gene Segments Rearranged in Vitro", J. Mol. Biol. vol. 227, pp. 381-388, 1992.
Hoogenboom et al. "Construction and Expression of Antibody-Tumor Necrosis Factor Fusion Proteins", Mol. Immunol. vol. 28, No. 9, pp. 1027-1037, 1991.
Hudson et al. "Engineered Antibodies" Nature Med. vol. 9, pp. 129-134, 2003.
Hurle et al. "Protein Engineering Techniques for Antibody Humanization", Current Opinion Biotech.: 5: 428-433, 1994.

Huston et al. "Protein Engineering of Antibody Binding Sites: Recovery of Specific Activity in an Anti-Digoxin Single-Chain Fv Analogue Produced in *Escherichial coli* ", PNAS (USA); vol. 85, pp. 5879-5883, 1988.
Idusogie et al. "Mapping of the C1q Binding Site on Rituxan, a Chimeric Antibody with a Human IgG1 Fc", J. Immunol. vol. 164: 4178-4184, 2000.
Jackson et al. "In Vitro Antibody Maturation", J. Immunol: 154:3310-3319, 1995.
Jakobovits et al. "Analysis of Homozygous Mutant Chimeric Mice: Deletion of the Immunoglobulin Heavy-Chain Joining Region Blocks B-cell Development and Antibody Production" Proc. Natl. Acad. Sci. USA; vol. 90, pp. 2551-2555, 1993.
Jakobovits et al. "Gerin-line Transmission and Expression of a Human-derived Yeast Artificial Chromosome", Nature, vol. 362, pp. 255-258, 1993.
Johnson et al. "The Kabat Database and a Bioinformatics Example", Methods in Molecular Biology; vol. 248, pp. 11-25, 2003.
Jones et al. "Replacing the Complementarity-Determining Regions in a Human Antibody with those from a mouse" Nature, vol. 321, pp. 522-525, 1986.
Kaufman et al. "Amplification and Expression of Sequences Cotransfected with a Modular Dihydrofolate Reductase Complementary DNA Gene", J. Mol. Biol. 159: 601-621, 1982.
Keown et al. "Methods for Introducing DNA into Mammalian Cells", Methods in Enzymology: 185:527-537, 1990.
Kohler et al. "Continuous Cultures of Fused Cells Secreting Antibody of Predefined Specificity", Nature, vol. 256, pp. 495-497, 1975.
Kostelny et al. "Formation of a Bispecific Antibody by the Use of Leucine Zippers" J. Immunol. 148(5):1547-1553, 1992.
Kozbor et al. "A Human Hybrid Myeloma for Production of Human Monoclonal Antibodies", Journal Immunology 133:3001, 1984.
Lee et al. "High-affinity Human Antibodies from Phage-displayed Synthetic Fab Libraries with a Single Framework Scaffold", J. Mol. Biol. 340, 1073-1093, 2004.
Lee et al. "Bivalent Antibody Phage Display Mimics Natural Immunoglobulin", J Immunoligical Methods :284, pp. 119-132, 2004.
Li et al. "Human Antibodies for Immunotherapy Development Generated via a Human B Cell Hybridoma Technology", PNAS (USA) vol. 103, pp. 3557-3562, 2006.
Lonberg et al. "Antigen-Specific Human Antibodies from Mice Comprising Four Distinct Genetic Modifications", Nature: vol. 368, pp. 856-859, 1994.
Lonberg et al. "Human Antibodies from Transgenic Mice" , Intern. Rev. Immunol. vol. 13, pp. 65-93, 1995.
Lubiniecki et al. "Advances in Animal Cell Biology and Technology for Bioprocesses", ESACT pp. 442-451, 1989.
Luckow et al. "Trends in the Development o fBaculovirus Expression Vectors", Biotechnology, vol. 6, pp. 47-55, 1988.
Maeda et al. "Production of Human α-interferon in Silkworm Using a Baculovirus Vector", Nature, vol. 315, pp. 592-594, 1985.
Mantei et al. "Rabbit β-globin Mrna Production in Mouse L Cells Transformed with Cloned Rabbit β-globin Chromosomal DNA", Nature, 281:40-46, 1979.
Mansour et al. "Disruption of the Proto-Oncogene *int*-2 in Mouse Embryo-Derived Stem Cells: a General Strategy for Targeting Mutations to Non-selectable Genes", Nature, 336:348-352, 1988.
Marks et al. "By-passing Immunization Human Antibodies from V-gene Libraries Displayed, on Phage" J. Mol. Biol. vol. 222, pp. 581-597, 1991.
Marks et al. "By-passing Immunization: Building High Affinity Human Antibodies by Chain Shuffling" Biotechnology; vol. 10 pp. 779-783, 1992.
Mather, J.P. "Establishment and Characterization of Two Distinct Mouse Testicular Epithelial Cell Lines" Biology of Reproduction 23, p. 243-252 ,1980.
Mather et al. "Culture of Testicular Cells in Hormone-Supplemented Serum-Free Medium", NYAS ; vol. 0383-0044, p. 44, 1982.
Maxam et al. "Sequencing End-Labeled DNA with Base-Specific Chemical Cleavages", Methods in Enzymology, 65:499, 1980.
McCafferty et al. "Phage Antibodies: Filamentous Phage Displaying Antibody Variable Domains", Nature, 348:552-554, 1990.

Messing et al. "A System for Shotgun DNA Sequencing", Nuceleic Acids Research 9:309, 1981.

Miller et al. Genetic. Engineering Setlow; Penum Publishing; vol. 8, pp. 277-279, 1986.

Millstein et al. "Hybrid Hybridomas and their use in Immunohistochemistry", Nature vol. 305:537-539, 1983.

Morimoto et al. Single-step Purification of F(ab')$^2$ Journal of Biochemical and Biophysical Methods 24:107-117,1992.

Morrison S.L. "Success in Specification" Nature, vol. 368, pp. 812-813, 1994.

Morrison et al. "Chimeric Human Antibody Molecules: Mouse Antigen-binding Domains with Human Constant Region Domains", Proc. Natl. Acad. Sci.USA, vol. 81, pp. 6851-6855,1984.

Neuberger M. "Generating High-Avidity Human Mabs in Mice", Nature, vol. 14, p. 826, 1996.

Pluckthun, A. "The Pharmacology of Monoclonal Antibodies", Springer-Verlag vol. 113, pp. 269-315, 1994.

Presta, L.G. "Antibody Engineering" Current Opinion in Struct Biol. 2:593-596, 1992.

Presta et al. "Humanization of an Antibody Directed Against IgE", J. Immnol., 151:2623-2632, 1993.

Ravetch et al. "Fc Receptors", Annu. Rev. Immunol. 9: 457-92, 1991.

Riechmann et al. "Reshaping Human Antibodies for Therapy", Nature, vol. 332, pp. 323-329, 1988.

Schier et al. "Identification of Functional and Structural Amino-Acid Residues by Parsimonious Mutagenesis", Gene, 169, pp. 147-155, 1996.

Shalaby et al. "Development of Humanized Bispecific Antibodies Reactive with Cytotoxic Lymphocytes and Tumor Cells Overexpressing the HER2 Protooncogene", J. Exp. Med. 175:217-225,1992.

Shaw et al. "A General Method for the Transfer of Cloned Genes to Plant Cells", Gene 23:315, 1983.

Sheets et al. "Efficient Construction of a large Nonimmune Phage Antibody Library: The Production of High-Affinity Human Single-Chain Antibodies to Protein Antigens", PNAS (USA) vol. 95, pp. 6157-6162, 1998.

Sheriff et al. "Redefining the Minimal Antigen-Binding Frgament", Nature Structural Biology vol. 3, pp. 733-736, 1996.

Shields et al. "High Resolution Mapping of the Binding Site on Human IgG1 for FcYRI, FCYRI, FCYRII, and FCYRIII and FcRn Design of IgG1 Variants with Improved Binding to the FCYR"; J. Biol. Chem. vol. 276, No. 9, pp. 6591-6604, 2001.

Sidhu et al. "Phage-displayed antibody libraries of synthetic heavy chain complementarity determining regions" J. Mol . . . Biol. vol. 338, No. 2, pp. 299-310, 2004.

Simonsen et al. "Isolation and expression of an altered mouse dihydrofolate reductase cDNA" Proc. Natl. Acad. Sci. USA, vol. 80, pp. 249-2499, 1983.

Sims et al. "A Humanized CD18 Antibody Can Block Function without Cell Destruction", Journal Immunol., 151:2296 ,1993.

Stamenkovic et al. "The B Lymphocyte Adhesion Molecule CD22 Interacts with Leukocyte Common Antigen CD45RO on T Cells and α2-6 Sialyltransferase, CD75, on B Cells" Cell vol. 66, 1133-1144, 1991.

Thomas, P. "Hybridization of Denatured RNA and small DNA Fragments Transferred to Nitrocellulose"; Proc. Natl. Acad. Sci. USA: 77:5201-5205, 1980.

Traunecker et al. "Bispecific Single Chain Molecules (Janusins) target Cytotoxic Lymphocytes on HIV Infected Cells" , EMBO Journal vol. 10 No. 12 , pp. 3655-3659, 1991.

Trill et al. "Production of Monoclonal Antibodies in COS and CHO cells", Current Opinion Biotech 6:553-560, 1995.

Tutt et al. "Trispecific F(ab')$_3$ Derivatives that Use Cooperative Signaling via the TCR/CD3 Complex and CD2 to Activate and Redirect Resting Cytotoxic T Cells$_1$" J. Immunol: 147:60-69, 1991.

Urlaub et al. "Isolation of Chinese Hamster Cell Mutants Deficient in Dihydrofolate Reductase Activity" Proc. Natl. Acad. Sci. USA vol. 77, No. 7, p. 4216-4220, 1980.

Van Dijk et al. "Human Antibodies as Next Generation Therapeutics" Current Opinion in Chem. Biol. 5:368-374, 2001.

Vaswani et al. "Humanized antibodies as potential therapeutic drugs", Ann Allergy Asthma Immunol. 81: 105-119, 1998.

Vaughan et al. "Human antibodies with sub-nanomolar affinities isolated from a large non-immunized phage display libraby", Nature Biotechnology, vol. 14, pp. 309-314, 1996.

Verhoeyen et al. "Reshaping Human Antibodies: Grafting an Antilysozyme Activity", Science, 239:1534-1536, 1988.

Ward et al. "Binding activities of a repertoire of single immunoglobulin variable domains,secreted from *Escherichia coli*", Nature, vol. 341, pp. 544-546, 1989.

Waterhouse et al. "Combinatorial Infection and in Vivo Recombination: a Strategy for Making Large Phage Antibody Repertoires", Nuc. Acids. Res., 21:2265-2266, 1993.

Zhaolie, Chen :"Substitution of Asparagine for Glutamine for the Cultivation of Recombinant CHO Cell Line Producing Prourokinase"; Biotechnology Information, No. 2, pp. 25-27, published Feb. 28, 2001 (English translation).

* cited by examiner

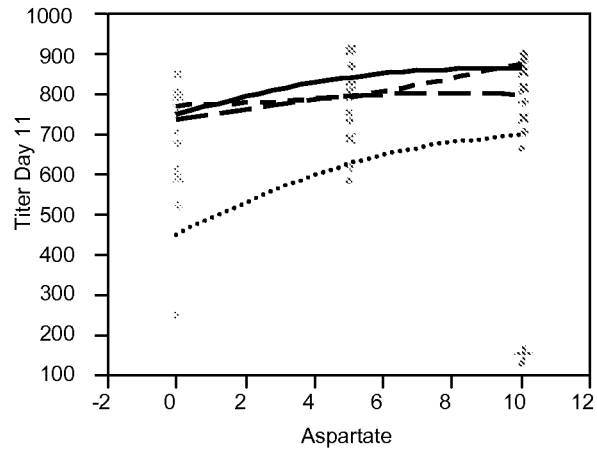

Bivariate Fit of Titer Day 11 By Aspartate Glutamine=0

······ Smoothing Spline Fit, lambda=1 Asparagine==2.5
—— Smoothing Spline Fit, lambda=1 Asparagine==7.5
— — Smoothing Spline Fit, lambda=1 Asparagine==10
—— Smoothing Spline Fit, lambda=1 Asparagine==15

Smoothing Spline Fit, lambda=1 Asparagine==2.5

R-Square                 0.573894
Sum of Squares Error     73461.63

Smoothing Spline Fit, lambda=1 Asparagine==7.5

R-Square                 0.65596
Sum of Squares Error     11556.31

Smoothing Spline Fit, lambda=1 Asparagine==10

R-Square                 0.408718
Sum of Squares Error     25684.65

Smoothing Spline Fit, lambda=1 Asparagine==15

R-Square                 0.220438
Sum of Squares Error     26400.64

FIG. 5

PRODUCTION OF PROTEINS IN GLUTAMINE-FREE CELL CULTURE MEDIA

RELATED APPLICATIONS

This application claims the benefit under 35 USC §119 to U.S. Provisional Application 61/232,889 filed Aug. 11, 2009.

FIELD OF THE INVENTION

The present invention relates generally to glutamine-free cell culture media. The invention further concerns the production of recombinant proteins, such as antibodies, in glutamine-free mammalian cell culture.

BACKGROUND OF THE INVENTION

Mammalian cells have become the dominant system for the production of mammalian proteins for clinical applications, primarily due to their ability to produce properly folded and assembled heterologous proteins, and their capacity for post-translational modifications. It is conventional to have glutamine in cell culture media during recombinant production of heterologous proteins, including antibodies. L-glutamine is an essential amino acid, which is considered the primary energy and nitrogen sources for cells in culture. Most commercially available media are formulated with free L-glutamine which is either included in the basal formula or added to liquid media formulations at the time of use. Thus, all mammalian cell culture media contain glutamine except those for glutamine synthetase transfected cell lines, such as GS NS0 and GS CHO cell lines, where the cells themselves produce the glutamine needed for growth. Glutamine is widely used at various concentrations typically from 1 to 20 mM in base media and much higher concentration in feeds for fed-batch process. For example, the concentration of L-glutamine is 0.5 mM in Ames' Medium and 10 mM in MCDP Media 131. DMEM/Ham's Nutrient Mixture F-12 (50:50) is often used as a starting formulation for proprietary media used with Chinese Hamster Ovary (CHO) cells. L-glutamine in DMEM/Ham's Nutrient Mixture F-12 is 2.5 mM. L-glutamine concentration in Serum-Free/Protein Free Hybridoma Medium is 2.7 mM. L-glutamine in DMEM, GMEM, IMDM and H-Y medium is 4 mM, of which IMDM is often used as a starting formulation for proprietary hybridoma cell culture media. It is generally held that hybridoma cells grow better in concentrations of L-glutamine that are above the average levels found in media. (Dennis R. Conrad, Glutamine in Cell Culture, Sigma-Aldrich Media Expert)

It was shown that glutamine is the main source of ammonia accumulated in cell culture (see review by Markus Schneider, et. al. 1996, *Journal of Biotechnology* 46:161-185). Thus, lowering glutamine in cell culture media significantly reduced the accumulation of $NH_4^+$ level, resulting in lower cytotoxicity (see Markus Schneider, et. al. 1996, supra). Reduced $NH_4^+$ cytotoxicity resulted in higher cell viability, thus extended culture longevity. Based on an estimated glutamine consumption study using CHO cells, it was suggested that cells may consume glutamine at a rate of 0.3-0.4 mM per day (Miller, et. al. 1988, Biotechnol. Bioeng. 32: 947-965). Altamirano et al. (2001, *J. Biotechnol.* 110:171-9) studied the effect of glutamine replacement by glutamate and the balance between glutamate and glucose metabolism on the redistribution of CHO cells producing recombinant human tissue plasminogen activator (rhut-PA). When glutamine was replaced with glutamate and balanced with glucose catabolism (carbon and nitrogen ratio, C/N ratio), cell metabolism was found redistributed and forced to utilize carbon and energy source more favorably to production of rhut-PA. It was also reported that CHO cells in adherent cultures can grow in the absence of added glutamine due to endogenous glutamine synthetase activity that allowed cells to synthesize glutamine from glutamic acid in the medium (Sanfeliu and Stephanopoulos, 1999, *Biotechnol. Bioeng.* 64:46-53). However, compared to control cultures in glutamine-containing media, the cell growth rate in glutamine-free media was slower with an increased fraction of cells distributed in the G0/G1 phase. The depletion of both glutamine and glutamic acid did cause cell death.

SUMMARY OF THE INVENTION

The present invention is based, at least in part, on the unexpected finding that not only can recombinant proteins be produced in a mammalian host cell using a glutamine-free production medium without any significant adverse effect, in fact the use of a glutamine-free medium in the production phase significantly increases cell viability, culture longevity, specific productivity and/or the final recombinant protein titer.

The present invention is also based on the unexpected finding that the addition of asparagine to a glutamine-free production medium can further enhance the cell viability, culture longevity, specific productivity and/or the final recombinant protein titer in a mammalian host cell using a glutamine-free production medium without any significant adverse effect.

In one aspect, the invention concerns a process for producing a polypeptide in a mammalian host cell expressing said polypeptide, comprising culturing the mammalian host cell in a production phase of the culture in a glutamine-free production culture medium supplemented with asparagine.

In one embodiment, the mammalian host cell is a Chinese Hamster Ovary (CHO) cell.

In another embodiment, the mammalian host cell is a dhfr⁻ CHO cell.

In yet another embodiment, the production medium is serum-free.

In a further embodiment, the production culture medium comprises one or more ingredients selected from the group consisting of
1) an energy source;
2) essential amino acids;
3) vitamins;
4) free fatty acids; and
5) trace elements.

In a still further embodiment, wherein the production culture medium additionally comprises one or more ingredients selected from the group consisting of:
1) hormones and other growth factors;
2) salts and buffers; and
3) nucleosides.

In all embodiments, the production phase may, for example, be a batch or fed batch culture phase.

In all embodiments, the process may further comprise the step of isolating said polypeptide.

In a further embodiment, isolation may be followed by determining one or more of cell viability, culture longevity, specific productivity and final recombinant protein titer following isolation.

In a still further embodiment, at least one of the cell viability, culture longevity, specific productivity and final recombinant protein titer is increased relative to the same polypeptide produced in a glutamine-containing production medium of the same composition.

In a further aspect, the invention concerns a ready-to-use glutamine-free cell culture medium for the production of a polypeptide in a production phase.

In yet another embodiment, the polypeptide is a mammalian glycoprotein.

In other embodiments, the polypeptide is selected from the group consisting of antibodies, antibody fragments, and immunoadhesins.

In all embodiments, the polypeptide may, for example, be an antibody, or a biologically functional fragment of an antibody. Representative antibody fragments include Fab, Fab', F(ab')$_2$, scFv, (scFv)$_2$, dAb, complementarity determining region (CDR) fragments, linear antibodies, single-chain antibody molecules, minibodies, diabodies, and multispecific antibodies formed from antibody fragments.

In a still further embodiment, the antibody or antibody fragment is chimeric, humanized or human.

Therapeutic antibodies include, without limitation, anti-HER2 antibodies anti-CD20 antibodies; anti-IL-8 antibodies; anti-VEGF antibodies; anti-CD40 antibodies, anti-CD11a antibodies; anti-CD18 antibodies; anti-IgE antibodies; anti-Apo-2 receptor antibodies; anti-Tissue Factor (TF) antibodies; anti-human a43$_7$ integrin antibodies; anti-EGFR antibodies; anti-CD3 antibodies; anti-CD25 antibodies; anti-CD4 antibodies; anti-CD52 antibodies; anti-Fc receptor antibodies; anti-carcinoembryonic antigen (CEA) antibodies; antibodies directed against breast epithelial cells; antibodies that bind to colon carcinoma cells; anti-CD38 antibodies; anti-CD33 antibodies; anti-CD22 antibodies; anti-EpCAM antibodies; anti-GpIIb/IIIa antibodies; anti-RSV antibodies; anti-CMV antibodies; anti-HIV antibodies; anti-hepatitis antibodies; anti-CA 125 antibodies; anti-$\alpha v \beta 3$ antibodies; anti-human renal cell carcinoma antibodies; anti-human 17-1A antibodies; anti-human colorectal tumor antibodies; anti-human melanoma antibody R24 directed against GD3 ganglioside; anti-human squamous-cell carcinoma; and anti-human leukocyte antigen (HLA) antibodies, and anti-HLA DR antibodies.

In other embodiments, the therapeutic antibody is an antibody binding to a HER receptor, VEGF, IgE, CD20, CD11a, CD40, or DR5.

In other embodiments, the therapeutic antibody is an anti-BR3 antibody or BR3-Fc immunoadhesin.

In other embodiments of the method of the present invention, the polypeptide expressed in the recombinant host cell is a therapeutic polypeptide. For example, the therapeutic polypeptide can be selected from the group consisting of a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-$\beta$; platelet-derived growth factor (PDGF); fibroblast growth factor such as aFGF and bFGF; epidermal growth factor (EGF); transforming growth factor (TGF) such as TGF-alpha and TGF-beta, including TGF-$\beta 1$, TGF-$\beta 2$, TGF-$\beta 3$, TGF-$\beta 4$, or TGF-$\beta 5$; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20, CD34, and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD 18, an ICAM, VLA-4 and VCAM; a tumor associated antigen such as HER2, HER3 or HER4 receptor; and fragments of said polypeptides.

In all embodiments, the recombinant host cell can be an eukaryotic host cell. such as a mammalian host cell, including, for example, Chinese Hamster Ovary (CHO) cells.

These and other aspects will be apparent from the description below, including the Examples and the appended claims.

BRIEF DESCRIPTION OF THE DRAWINGS

FIG. 5. Apomab antibody titer production across various Asparagine and Aspartate concentrations in Glutamine-free and low Glutamate conditions. A positive titration effect was observed when increasing Aspartate from 0 to 10 mM under these conditions.

DETAILED DESCRIPTION OF THE INVENTION

A. Definitions

Figure 1:
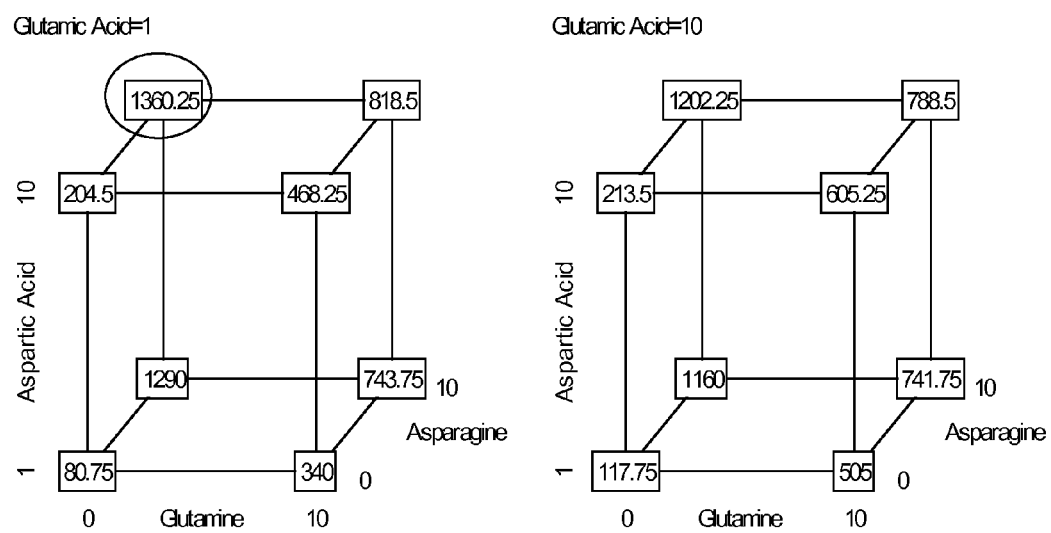
FIG. 1. Apomab antibody cube plot analysis of titer results from a Full Factorial Design of Experiment (DOE) evaluating the effect of different concentrations of Glutamine, Glutamate, Asparagine and Aspartate. The model predicts that the highest titer is achieved in Glutamine-Free media supplemented with 10 mM Asparagine, 10 mM Aspartic Acid and 1 mM Glutamic Acid.

The terms "cell culture medium", "culture medium", and "nutrient mixture" refer to a nutrient solution used for growing mammalian cells that typically provides at least one component from one or more of the following categories:
1) an energy source, usually in the form of a carbohydrate such as glucose;
2) some or all of the essential amino acids, and usually the basic set of twenty amino acids plus cystine;
3) vitamins and/or other organic compounds typically required at low concentrations;
4) free fatty acids; and
5) trace elements, where trace elements are defined as inorganic compounds or naturally occurring elements that are typically required at very low concentrations, usually in the micromolar range.

The nutrient mixture may optionally be supplemented with one or more component from any of the following categories:
1) hormones and other growth factors as, for example, insulin, transferrin, and epidermal growth factor;
2) salts and buffers as, for example, calcium, magnesium, and phosphate; and
3) nucleosides such as, for example, adenosine and thymidine.

The cell culture medium is generally "serum free" when the medium is essentially free of serum from any mammalian source (e.g. fetal bovine serum (FBS)). By "essentially free" is meant that the cell culture medium comprises between about 0-5% serum, preferably between about 0-1% serum, and most preferably between about 0-0.1% serum. Advantageously, serum-free "defined" medium can be used, wherein the identity and concentration of each of the components in the medium is known (i.e., an undefined component such as bovine pituitary extract (BPE) is not present in the culture medium).

In the context of the present invention the expressions "cell", "cell line", and "cell culture" are used interchangeably, and all such designations include progeny. Thus, the words "transformants" and "transformed (host) cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "animal host cell," "animal cell," "animal recombinant host cell," and the like, encompasses invertebrate, non-mammalian vertebrate (e.g., avian, reptile and amphibian) and mammalian cells. Examples of invertebrate cells include the following insect cells: *Spodoptera frugiperda* (caterpillar), *Aedes aegypti* (mosquito), *Aedes albopictus* (mosquito), *Drosophila melanogaster* (fruitfly), and *Bombyx mori*. See, e.g., Luckow et al., Bio/Technology, 6:47-55 (1988); Miller et al., in *Genetic Engineering*, Setlow, J. K. et al., eds., Vol. 8 (Plenum Publishing, 1986), pp. 277-279; and Maeda et al., *Nature*, 315:592-594 (1985).

The term "mammalian host cell," "mammalian cell," "mammalian recombinant host cell," and the like, refer to cell lines derived from mammals that are capable of growth and survival when placed in either monolayer culture or in suspension culture in a medium containing the appropriate nutrients and growth factors. The necessary nutrients and growth factors for a particular cell line are readily determined empirically without undue experimentation, as described for example in *Mammalian Cell Culture* (Mather, J. P. ed., Plenum Press, N. Y. (1984)), and by Barnes and Sato (*Cell*, 22:649 (1980)). Typically, the cells are capable of expressing and secreting large quantities of a particular protein of interest (typically a recombinant protein) into the culture medium, and are cultured for this purpose. However, the cells may be cultured for a variety of other purposes as well, and the scope of this invention is not limited to culturing the cells only for production of recombinant proteins. Examples of suitable mammalian cell lines, capable of growth in the media of this invention, include monkey kidney CVI line transformed by SV40 (COS-7, ATCC® CRL 1651); human embryonic kidney line 293S (Graham et al., *J. Gen. Virolo.*, 36:59 (1977)); baby hamster kidney cells (BHK, ATCC® CCL 10); mouse sertoli cells (TM4, Mather, *Biol. Reprod.*, 23:243 (1980)); monkey kidney cells (CVI-76, ATCC® CCL 70); African green monkey kidney cells (VERO-76, ATCC® CRL-1587); human cervical carcinoma cells (HELA, ATCC® CCL 2); canine kidney cells (MDCK, ATCC® CCL 34); buffalo rat liver cells (BRL 3A, ATCC® CRL 1442); human lung cells (W138, ATCC® CCL 75); human liver cells (Hep G2, HB 8065); mouse mammary tumor cells (MMT 060562, ATCC® CCL 5I); rat hepatoma cells (HTC, MI.54, Baumann et al., J. Cell Biol., 85:1 (1980)); and TR-1 cells (Mather et al., *Annals N.Y. Acad. Sci.*, 383:44 (1982)) and hybridoma cell lines. Chinese hamster ovary cells (Urlab and Chasin, *Proc. Natl. Acad. Sci. USA*, 77:4216 (1980)) are a preferred cell line for practicing this invention. CHO cells suitable for use in the methods of the present invention have also been described in the following documents: EP 117,159, published Aug. 29, 1989; U.S. Pat. Nos. 4,766,075; 4,853,330; 5,185,259; Lubiniecki et al., in *Advances in Animal Cell Biology and Technology for Bioprocesses*, Spier et al., eds. (1989), pp. 442-451. Known CHO derivatives suitable for use herein include, for example, CHO/-DHFR (Urlaub and Chasin, *Proc. Natl. Acad. Sci. USA*, 77: 4216 (1980)), CHO-K1 DUX B11 (Simonsen and Levinson, *Proc. Natl. Acad. Sci. USA* 80: 2495-2499 (1983); Urlaub and Chasin, supra), and dp 12.CHO cells (EP 307,247 published Mar. 15, 1989). Preferred host cells include CHO-K1 DUX B11 and dp 12.CHO cells.

"dhfr⁻ CHO cell" refers to a dihydrofolate reductase (DHFR) deficient CHO cell. Production of recombinant proteins in mammalian cells has allowed the manufacture of a number of large, complex glycosylated polypeptides for clinical applications. Chinese hamster ovary (CHO) DHFR– cells and the amplifiable selectable marker DHFR are routinely used to establish cell lines that produce clinically useful amounts of product. (Urlab, G. and Chasin, L. A. (1980) Proc. Natl Acad. Sci. USA, 77, 4216-4220; Kaufman, R. J. and Sharp, P. (1982) J. Mol. Biol., 159, 601-621; Gasser, C. S., Simonsen, C. S., Schilling, J. W. and Schmike, R. T. (1982) Proc. Natl Sci. USA, 79, 6522-6526)

By "phase" is meant a certain phase of culturing of the cells as is well recognized by the practitioner.

"Growth phase" of the cell culture refers to the period of exponential cell growth (the log phase) where cells are generally rapidly dividing. During this phase, cells are cultured for a period of time, usually between 1-4 days, and under such conditions that cell growth is maximized. The growth cycle for the host cell can be determined for the particular host cell envisioned without undue experimentation. During the growth phase, cells are cultured in nutrient medium containing the necessary additives generally at about 30-40° C., preferably about 37° C., in a humidified, controlled atmosphere, such that optimal growth is achieved for the particular cell line. Cells are maintained in the growth phase for a period of between about one and four days, usually between about two and three days.

"Transition phase" of the cell culture refers to the period of time during which culture conditions for the production phase are engaged. During the transition phase environmental factors such as temperature are shifted from growth conditions to production conditions.

"Production phase" of the cell culture refers to the period of time during which cell growth has plateaued. During the production phase, logarithmic cell growth has ended and protein production is primary. During this period of time the medium is generally supplemented to support continued protein production and to achieve the desired protein product.

The phrase "fed batch cell culture" when used herein refers to a batch culture wherein the animal (e.g. mammalian) cells and culture medium are supplied to the culturing vessel initially and additional culture nutrients are fed, continuously or in discrete increments, to the culture during culturing, with or without periodic cell and/or product harvest before termination of culture. Fed batch culture includes "semi-continuous fed batch culture" wherein periodically whole culture (including cells and medium) is removed and replaced by fresh medium. Fed batch culture is distinguished from simple "batch culture" in which all components for cell culturing (including the animal cells and all culture nutrients) are supplied to the culturing vessel at the start of the culturing process. Fed batch culture can be further distinguished from perfusion culturing insofar as the supernatant is not removed from the culturing vessel during the process (in perfusion culturing, the cells are restrained in the culture by, e.g., filtration, encapsulation, anchoring to microcarriers etc and the culture medium is continuously or intermittently introduced and removed from the culturing vessel). However, removal of samples for testing purposes during fed batch cell culture is contemplated.

When used herein, the term "glutamine" refers to the amino acid L-glutamine (also known as "Gln" and "Q" by three-letter and single-letter designation, respectively) which is recognized as both an amino acid building block for protein synthesis and as an energy source in cell culture. Thus, the terms "glutamine" and "L-glutamine" are used interchangeably herein.

The word "glucose" refers to either of α-D-glucose or β-D-glucose, separately or in combination. It is noted that α and β glucose forms are interconvertible in solution.

The expression "osmolality" is a measure of the osmotic pressure of dissolved solute particles in an aqueous solution. The solute particles include both ions and non-ionized molecules. Osmolality is expressed as the concentration of osmotically active particles (i.e., osmoles) dissolved in 1 kg of water (1 mOsm/kg $H_2O$ at 38° C. is equivalent to an osmotic pressure of 19 mm Hg). "Osmolarity" refers to the number of solute particles dissolved in 1 liter of solution. Solutes which can be added to the culture medium so as to increase the osmolality thereof include proteins, peptides, amino acids, non-metabolized polymers, vitamins, ions, salts, sugars, metabolites, organic acids, lipids, etc. In the preferred embodiment, the concentration of amino acids and NaCl in the culture medium is increased in order to achieve the desired osmolality ranges set forth herein. When used herein, the abbreviation "mOsm" means "milliosmoles/kg $H_2O$".

The term "cell density" as used herein refers to that number of cells present in a given volume of medium.

The term "cell viability" as used herein refers to the ability of cells in culture to survive under a given set of culture conditions or experimental variations. The term as used herein also refers to that portion of cells which are alive at a particular time in relation to the total number of cells, living and dead, in the culture at that time.

The terms "amino acids" and "amino acid" refer to all naturally occurring alpha amino acids in both their D and L stereoisomeric forms, and their analogs and derivatives. An analog is defined as a substitution of an atom in the amino acid with a different atom that usually has similar properties. A derivative is defined as an amino acid that has another molecule or atom attached to it. Derivatives would include, for example, acetylation of an amino group, amination of a carboxyl group, or oxidation of the sulfur residues of two cysteine molecules to form cystine.

The term "protein" is meant to refer to a sequence of amino acids for which the chain length is sufficient to produce the higher levels of tertiary and/or quaternary structure. This is to distinguish from "peptides" or other small molecular weight drugs that do not have such structure. Typically, the protein herein will have a molecular weight of at least about 15-20 kD, preferably at least about 20 kD. Examples of proteins encompassed within the definition herein include all mammalian proteins, in particular, therapeutic and diagnostic proteins, such as therapeutic and diagnostic antibodies, and, in general proteins that contain one or more disulfide bonds, including multi-chain polypeptides comprising one or more inter- and/or intrachain disulfide bonds.

The term "therapeutic protein" or "therapeutic polypeptide" refers to a protein that is used in the treatment of disease, regardless of its indication or mechanism of action. In order for therapeutic proteins to be useful in the clinic it must be manufactured in large quantities. "Manufacturing scale" production of therapeutic proteins, or other proteins, utilize cell cultures ranging from about 400 L to about 80,000 L, depending on the protein being produced and the need. Typically such manufacturing scale production utilizes cell culture sizes from about 400 L to about 25,000 L. Within this range, specific cell culture sizes such as 4,000 L, about 6,000 L, about 8,000, about 10,000, about 12,000 L, about 14,000 L, or about 16,000 L are utilized.

As used herein, "polypeptide of interest" refers generally to peptides and proteins having more than about ten amino acids. The polypeptides may be homologous to the host cell, or preferably, may be exogenous, meaning that they are heterologous, i.e., foreign, to the host cell being utilized, such as a human protein produced by a non-human mammalian, e.g., Chinese Hamster Ovary (CHO) cell. Preferably, mammalian polypeptides (polypeptides that were originally derived from a mammalian organism) are used, more preferably those which are directly secreted into the medium. The term "polypeptide" or "polypeptide of interest" specifically includes antibodies, in particular, antibodies binding to mammalian polypeptides, such as any of the mammalian polypeptides listed below or fragments thereof, as well as immunoadhesins (polypeptide-Ig fusion), such as those comprising any of the mammalian polypeptides listed below, or fragments thereof.

Examples of mammalian polypeptides include, without limitation, transmembrane molecules (e.g. receptors) and ligands such, as growth factors. Exemplary polypeptides include molecules such as renin; a growth hormone, including human growth hormone and bovine growth hormone; growth hormone releasing factor; parathyroid hormone; thyroid stimulating hormone; interferon such as interferon-α, -β, and -γ; lipoproteins; α-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA), including t-PA variants; bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-α); a serum albumin such as human serum albumin; Muellerian-inhibiting substance; relaxin A-chain; relaxin B-chain; prorelaxin; mouse gonadotropin-associated peptide; a microbial protein, such as β-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20, CD34, CD40; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER1 (EGFR), HER2, HER3 or HER4 receptor; Apo2L/TRAIL, hedgehog, mitogen activated protein kinase (MAPK), and fragments of any of the above-listed polypeptides. Apo2L (TRAIL) and is variants are disclosed, for example, in U.S. Application Publication No. 20040186051. Anti-VEGF antibodies are disclosed, for example, in U.S. Pat. Nos. 8,994,879; 7,060,269; 7,169,901; and 7,297,334. Anti-CD20 antibodies are disclosed, for example, in U.S. Application Publication No. 20060246004. The BR3 polypeptide, anti-BR3 antibodies and BR3-Fc immunoadhesins are described, for example, in U.S. Application Publication No. 20050070689.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

As noted above, in certain embodiments, the protein is an antibody. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The term "antibody" is used in the broadest sense and specifically covers monoclonal antibodies (including full length antibodies which have an immunoglobulin Fc region or intact monoclonal antibodies), antibody compositions with polyepitopic specificity, polyclonal antibodies, multivalent antibodies, multispecific antibodies (e.g., bispecific antibodies) formed from at least two intact antibodies, diabodies, and single-chain molecules such as scFv molecules, as well as antibody fragments (e.g., Fab, F(ab')2, and Fv).

Unless indicated otherwise, the expression "multivalent antibody" is used throughout this specification to denote an antibody comprising three or more antigen binding sites. The multivalent antibody is typically engineered to have the three or more antigen binding sites and is generally not a native sequence IgM or IgA antibody.

The terms "full length antibody," "intact antibody" and "whole antibody" are used herein interchangeably to refer to an antibody in its substantially intact form, not antibody fragments as defined below. The terms particularly refer to an antibody with heavy chains that contain the Fc region.

"Antibody fragments" comprise only a portion of an intact antibody, generally including an antigen binding site of the intact antibody and thus retaining the ability to bind antigen. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., *Nature* 341, 544-546 (1989)) which consists of a VH domain; (vii) isolated CDR regions; (viii) F(ab')2 fragments, a bivalent fragment including two Fab' fragments linked by a disulphide bridge at the hinge region; (ix) single chain antibody molecules (e.g. single chain Fv; scFv) (Bird et al., *Science* 242: 423-426 (1988); and Huston et al., *PNAS (USA)* 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., *Proc. Natl. Acad. Sci. USA*, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. *Protein Eng.* 8(10):1057 1062 (1995); and U.S. Pat. No. 5,641,870).

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Single-chain Fv" or "scFv" antibody fragments comprise the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO93/1161; Hudson et al., (2003) Nat. Med. 9:129-134; and Hollinger et al., Proc. Natl. Acad. Sci. USA 90: 6444-6448 (1993). Triabodies and tetrabodies are also described in Hudson et al., (2003) Nat. Med. 9:129-134.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. Monoclonal antibodies are highly specific, being directed against a single antigen. In certain embodiments, a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations that typically include different antibodies directed against different determinants (epitopes), each monoclonal antibody is directed against a single determinant on the antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, Nature, 256:495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1991); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also, e.g., Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409. See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology. The humanized antibody may also include a Primatized™ antibody wherein the antigen-binding region of the antibody is derived from an antibody produced by immunizing macaque monkeys with the antigen of interest.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. Nature Biotechnology 14:309-314 (1996): Sheets et al. PNAS (USA) 95:6157-6162 (1998)); Hoogenboom and Winter, J. Mol. Biol., 227:381 (1991); Marks et al., J. Mol. Biol., 222:581 (1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368:812-13 (1994); Fishwild et al., Nature Biotechnology 14: 845-51 (1996); Neuberger, Nature Biotechnology 14: 826 (1996); Lonberg and Huszar, Intern. Rev. Immunol. 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., J. Immunol., 147 (1):86-95 (1991); and U.S. Pat. No. 5,750,373.

An "affinity matured" antibody is one with one or more alterations in one or more CDRs/HVRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al., Bio/Technology 10:779-783 (1992) describes affinity maturation by VH and VL domain shuffling. Random mutagenesis of CDR/HVR and/or framework residues is described by: Barbas et al., Proc Nat. Acad. Sci. USA 91:3809-3813 (1994); Schier et al., Gene 169:147-155 (1995); Yelton et al., J. Immunol. 155:1994-2004 (1995); Jackson et al., J. Immunol. 154(7):3310-9 (1995); and Hawkins et al., J. Mol. Biol. 226:889-896 (1992).

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions (HVRs) both in the light-chain and the heavy-chain variable domains. The more highly conserved portions of variable domains are called the framework regions (FRs). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody-dependent cellular toxicity.

The term "hypervariable region," "HVR," or "HV," when used herein refers to the amino acid residues of an antibody which are responsible for antigen-binding. For example, the term hypervariable region refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

The "light chains" of antibodies (immunoglobulins) from any vertebrate species can be assigned to one of two clearly distinct types, called kappa ($\kappa$) and lambda ($\lambda$), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG1, IgG2, IgG3, IgG4, IgA1, and IgA2. The heavy chain constant domains that correspond to the different classes of immunoglobulins are called $\alpha$, $\delta$, $\epsilon$, $\gamma$, and $\mu$, respectively. The subunit structures and three-dimensional configurations of different classes of immunoglobulins are well known and described generally in, for example, Abbas et al., Cellular and Mol. Immunology, 4th ed. (2000). An antibody may be part of a larger fusion molecule, formed by covalent or non-covalent association of the antibody with one or more other proteins or peptides.

The term "Fc region" is used to define the C-terminal region of an immunoglobulin heavy chain which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain.

By "Fc region chain" herein is meant one of the two polypeptide chains of an Fc region.

The "CH2 domain" of a human IgG Fc region (also referred to as "Cg2" domain) is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22:161-206 (1985). The CH2 domain herein may be a native sequence CH2 domain or variant CH2 domain.

The "CH3 domain" comprises the stretch of residues C-terminal to a CH2 domain in an Fc region. The CH3 region herein may be a native sequence CH3 domain or a variant CH3 domain (e.g. a CH3 domain with an introduced "protroberance" in one chain thereof and a corresponding introduced "cavity" in the other chain thereof; see U.S. Pat. No. 5,821,333, expressly incorporated herein by reference). Such variant CH3 domains may be used to make multispecific (e.g. bispecific) antibodies as herein described.

"Hinge region" herein may be a native sequence hinge region or a variant hinge region. The two polypeptide chains of a variant hinge region generally retain at least one cysteine residue per polypeptide chain, so that the two polypeptide chains of the variant hinge region can form a disulfide bond between the two chains. The preferred hinge region herein is a native sequence human hinge region, e.g. a native sequence human IgG1 hinge region.

A "functional Fc region" possesses at least one "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

An "intact" antibody is one which comprises an antigen-binding variable region as well as a light chain constant domain ($C_L$) and heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

A "parent antibody" or "wild-type" antibody is an antibody comprising an amino acid sequence which lacks one or more amino acid sequence alterations compared to an antibody variant as herein disclosed. Thus, the parent antibody generally has at least one hypervariable region which differs in amino acid sequence from the amino acid sequence of the corresponding hypervariable region of an antibody variant as herein disclosed. The parent polypeptide may comprise a native sequence (i.e. a naturally occurring) antibody (including a naturally occurring allelic variant), or an antibody with pre-existing amino acid sequence modifications (such as insertions, deletions and/or other alterations) of a naturally occurring sequence. Throughout the disclosure, "wild type," "WT," "wt," and "parent" or "parental" antibody are used interchangeably.

As used herein, "antibody variant" or "variant antibody" refers to an antibody which has an amino acid sequence which differs from the amino acid sequence of a parent antibody. Preferably, the antibody variant comprises a heavy chain variable domain or a light chain variable domain having an amino acid sequence which is not found in nature. Such variants necessarily have less than 100% sequence identity or similarity with the parent antibody. In a preferred embodiment, the antibody variant will have an amino acid sequence from about 75% to less than 100% amino acid sequence identity or similarity with the amino acid sequence of either the heavy or light chain variable domain of the parent antibody, more preferably from about 80% to less than 100%, more preferably from about 85% to less than 100%, more preferably from about 90% to less than 100%, and most preferably from about 95% to less than 100%. The antibody variant is generally one which comprises one or more amino acid alterations in or adjacent to one or more hypervariable regions thereof.

A "variant Fc region" comprises an amino acid sequence which differs from that of a native sequence Fc region by virtue of at least one amino acid modification. In certain embodiments, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide, e.g. from about one to about ten amino acid substitutions, and preferably from about one to about five amino acid substitutions in a native sequence Fc region or in the Fc region of the parent polypeptide. The variant Fc region herein will typically possess, e.g., at least about 80% sequence identity with a native sequence Fc region and/or with an Fc region of a parent polypeptide, or at least about 90% sequence identity therewith, or at least about 95% sequence or more identity therewith.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells and neutrophils; with PBMCs and NK cells being generally preferred. The effector cells may be isolated from a native source thereof, e.g. from blood or PBMCs as described herein.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, e.g., Daëron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology*, 15(7):637-640 (1997); Hinton et al., *J. Biol. Chem.* 279(8):6213-6216 (2004); WO 2004/92219 (Hinton et al.).

Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. *J. Biol. Chem.* 9(2):6591-6604 (2001).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. *J. Immunol.* 164: 4178-4184 (2000).

An "affinity matured" antibody is one with one or more alterations in one or more CDRs thereof which result an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

The term "therapeutic antibody" refers to an antibody that is used in the treatment of disease. A therapeutic antibody may have various mechanisms of action. A therapeutic antibody may bind and neutralize the normal function of a target associated with an antigen. For example, a monoclonal antibody that blocks the activity of the of protein needed for the survival of a cancer cell causes the cell's death. Another therapeutic monoclonal antibody may bind and activate the normal function of a target associated with an antigen. For example, a monoclonal antibody can bind to a protein on a cell and trigger an apoptosis signal. Yet another monoclonal antibody may bind to a target antigen expressed only on diseased tissue; conjugation of a toxic payload (effective agent), such as a chemotherapeutic or radioactive agent, to the monoclonal antibody can create an agent for specific delivery of the toxic payload to the diseased tissue, reducing harm to healthy tissue. A "biologically functional fragment" of a therapeutic antibody will exhibit at least one if not some or all of the biological functions attributed to the intact antibody, the function comprising at least specific binding to the target antigen.

The antibody may bind to any protein, including, without limitation, a member of the HER receptor family, such as HER1 (EGFR), HER2, HER3 and HER4; CD proteins such as CD3, CD4, CD8, CD19, CD20, CD21, CD22, and CD34; cell adhesion molecules such as LFA-1, Mol, p150,95, VLA-4, ICAM-1, VCAM and av/p3 integrin including either α or β or subunits thereof (e.g. anti-CD11a, anti-CD18 or anti-CD11b antibodies); growth factors such as vascular endothelial growth factor (VEGF); IgE; blood group antigens; flk2/flt3 receptor; obesity (OB) receptor; and protein C. Other exemplary proteins include growth hormone (GH), including human growth hormone (hGH) and bovine growth hormone (bGH); growth hormone releasing factor; parathyroid hormone; thyroid stimulating hormone; lipoproteins; α-1-antit-rypsin; insulin A-chain; insulin B-chain; proinsulin; follicle stimulating hormone; calcitonin; luteinizing hormone; glucagon; clotting factors such as factor VIIIC, factor, tissue factor, and von Willebrands factor; anti-clotting factors such as Protein C; atrial natriuretic factor; lung surfactant; a plasminogen activator, such as urokinase or tissue-type plasminogen activator (t-PA); bombazine; thrombin; tumor necrosis factor-α and -β; enkephalinase; RANTES (regulated on activation normally T-cell expressed and secreted); human macrophage inflammatory protein (MIP-1-α); serum albumin such as human serum albumin (HSA); mullerian-inhibiting substance; relaxin A-chain; relaxin B-chain; prorelaxin; mouse gonadotropin-associated peptide; DNase; inhibin; activin; receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I); insulin-like growth factor binding proteins (IGFBPs); erythropoietin (EPO); thrombopoietin (TPO); osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor (DAF); a viral antigen such as, for example, a portion of the AIDS envelope; transport proteins; homing receptors; addressins; regulatory proteins; immunoadhesins; antibodies; and biologically active fragments or variants of any of the above-listed polypeptides. Many other antibodies and/or other proteins may be used in accordance with the instant invention, and the above lists are not meant to be limiting.

Therapeutic antibodies of particular interest include those in clinical oncological practice or development such as commercially available AVASTIN® (bevacizumab), HERCEPTIN® (trastuzumab), LUCENTIS® (ranibizumab), RAPTIVA® (efalizumab), RITUXAN® (rituximab), and XOLAIR® (omalizumab), as well as, anti-amyloid beta (Abeta), anti-CD4 (MTRX1011A), anti-EGFL7 (EGF-like-domain 7), anti-IL13, Apomab (anti-DR5-targeted pro-apoptotic receptor agonist (PARA), anti-BR3 (CD268, BLyS receptor 3, BAFF-R, BAFF Receptor), anti-beta 7 integrin subunit, dacetuzumab (Anti-CD40), GA101 (anti-CD20 monoclonal antibody), MetMAb (anti-MET receptor tyrosine kinase), anti-neuropilin-1 (NRP1), ocrelizumab (anti-CD20 antibody), anti-OX40 ligand, anti-oxidized LDL (oxLDL), pertuzumab (HER dimerization inhibitors (HDIs), and. rhuMAb IFN alpha.

A "biologically functional fragment" of an antibody comprises only a portion of an intact antibody, wherein the portion retains at least one, and as many as most or all, of the functions normally associated with that portion when present in an intact antibody. In one embodiment, a biologically functional fragment of an antibody comprises an antigen binding site of the intact antibody and thus retains the ability to bind antigen. In another embodiment, a biologically functional fragment of an antibody, for example one that comprises the Fc region, retains at least one of the biological functions normally associated with the Fc region when present in an intact antibody, such as FcRn binding, antibody half life modulation, ADCC function and complement binding. In one embodiment, a biologically functional fragment of an antibody is a monovalent antibody that has an in vivo half life substantially similar to an intact antibody. For example, such a biologically functional fragment of an antibody may comprise an antigen binding arm linked to an Fc sequence capable of conferring in vivo stability to the fragment.

The term "diagnostic protein" refers to a protein that is used in the diagnosis of a disease.

The term "diagnostic antibody" refers to an antibody that is used as a diagnostic reagent for a disease. The diagnostic antibody may bind to a target antigen that is specifically associated with, or shows increased expression in, a particular disease. The diagnostic antibody may be used, for example, to detect a target in a biological sample from a patient, or in diagnostic imaging of disease sites, such as tumors, in a patient. A "biologically functional fragment" of a diagnostic antibody will exhibit at least one if not some or all of the biological functions attributed to the intact antibody, the function comprising at least specific binding to the target antigen.

"Purified" means that a molecule is present in a sample at a concentration of at least 80-90% by weight of the sample in which it is contained. The protein, including antibodies, which is purified is preferably essentially pure and desirably essentially homogeneous (i.e. free from contaminating proteins etc.).

An "essentially pure" protein means a protein composition comprising at least about 90% by weight of the protein, based on total weight of the composition, preferably at least about 95% by weight.

An "essentially homogeneous" protein means a protein composition comprising at least about 99% by weight of protein, based on total weight of the composition.

As used herein, "soluble" refers to polypeptides that, when in aqueous solutions, are completely dissolved, resulting in a clear to slightly opalescent solution with no visible particulates, as assessed by visual inspection. A further assay of the turbidity of the solution (or solubility of the protein) may be made by measuring UV absorbances at 340 nm to 360 nm with a 1 cm path-length cell where turbidity at 20 mg/ml is less than 0.05 absorbance units.

An "isolated" antibody or polypeptide is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

The terms "Protein A" and "ProA" are used interchangeably herein and encompasses Protein A recovered from a native source thereof, Protein A produced synthetically (e.g. by peptide synthesis or by recombinant techniques), and variants thereof which retain the ability to bind proteins which have a $C_H2/C_H3$ region, such as an Fc region. Protein A can be purchased commercially from Repligen, Pharmacia and Fermatech. Protein A is generally immobilized on a solid phase support material. The term "ProA" also refers to an affinity chromatography resin or column containing chromatographic solid support matrix to which is covalently attached Protein A.

The term "chromatography" refers to the process by which a solute of interest in a mixture is separated from other solutes in a mixture as a result of differences in rates at which the individual solutes of the mixture migrate through a stationary medium under the influence of a moving phase, or in bind and elute processes.

The term "affinity chromatography" and "protein affinity chromatography" are used interchangeably herein and refer to a protein separation technique in which a protein of interest or antibody of interest is reversibly and specifically bound to a biospecific ligand. Preferably, the biospecific ligand is covalently attached to a chromatographic solid phase material and is accessible to the protein of interest in solution as the solution contacts the chromatographic solid phase material. The protein of interest (e.g., antibody, enzyme, or receptor protein) retains its specific binding affinity for the biospecific ligand (antigen, substrate, cofactor, or hormone, for example) during the chromatographic steps, while other solutes and/or proteins in the mixture do not bind appreciably or specifically to the ligand. Binding of the protein of interest to the immobilized ligand allows contaminating proteins or protein impurities to be passed through the chromatographic medium while the protein of interest remains specifically bound to the immobilized ligand on the solid phase material. The specifically bound protein of interest is then removed in active form from the immobilized ligand with low pH, high pH, high salt, competing ligand, and the like, and passed through the chromatographic column with the elution buffer, free of the contaminating proteins or protein impurities that were earlier allowed to pass through the column. Any component can be used as a ligand for purifying its respective specific binding protein, e.g. antibody.

The terms "non-affinity chromatography" and "non-affinity purification" refer to a purification process in which affinity chromatography is not utilized. Non-affinity chromatography includes chromatographic techniques that rely on non-specific interactions between a molecule of interest (such as a protein, e.g. antibody) and a solid phase matrix.

A "cation exchange resin" refers to a solid phase which is negatively charged, and which thus has free cations for exchange with cations in an aqueous solution passed over or through the solid phase. A negatively charged ligand attached to the solid phase to form the cation exchange resin may, e.g., be a carboxylate or sulfonate. Commercially available cation exchange resins include carboxy-methyl-cellulose, sulphopropyl (SP) immobilized on agarose (e.g. SP-SEPHAROSE FAST FLOW™ or SP-SEPHAROSE HIGH PERFORMANCE™, from Pharmacia) and sulphonyl immobilized on agarose (e.g. S-SEPHAROSE FAST FLOW™ from Pharmacia). A "mixed mode ion exchange resin" refers to a solid phase which is covalently modified with cationic, anionic, and hydrophobic moieties. A commercially available mixed mode ion exchange resin is BAKERBOND ABX™ (J.T. Baker, Phillipsburg, N.J.) containing weak cation exchange groups, a low concentration of anion exchange groups, and hydrophobic ligands attached to a silica gel solid phase support matrix.

The term "anion exchange resin" is used herein to refer to a solid phase which is positively charged, e.g. having one or more positively charged ligands, such as quaternary amino groups, attached thereto. Commercially available anion exchange resins include DEAE cellulose, QAE SEPHADEX™ and FAST Q SEPHAROSE™ (Pharmacia).

A "buffer" is a solution that resists changes in pH by the action of its acid-base conjugate components. Various buffers which can be employed depending, for example, on the desired pH of the buffer are described in *Buffers. A Guide for the Preparation and Use of Buffers in Biological Systems*, Gueffroy, D., ed. Calbiochem Corporation (1975). In one embodiment, the buffer has a pH in the range from about 2 to about 9, alternatively from about 3 to about 8, alternatively from about 4 to about 7 alternatively from about 5 to about 7. Non-limiting examples of buffers that will control the pH in this range include MES, MOPS, MOPSO, Tris, HEPES, phosphate, acetate, citrate, succinate, and ammonium buffers, as well as combinations of these.

The "loading buffer" is that which is used to load the composition comprising the polypeptide molecule of interest and one or more impurities onto the ion exchange resin. The loading buffer has a conductivity and/or pH such that the polypeptide molecule of interest (and generally one or more impurities) is/are bound to the ion exchange resin or such that the protein of interest flows through the column while the impurities bind to the resin.

The "intermediate buffer" is used to elute one or more impurities from the ion exchange resin, prior to eluting the polypeptide molecule of interest. The conductivity and/or pH of the intermediate buffer is/are such that one or more impurity is eluted from the ion exchange resin, but not significant amounts of the polypeptide of interest.

The term "wash buffer" when used herein refers to a buffer used to wash or re-equilibrate the ion exchange resin, prior to eluting the polypeptide molecule of interest. Conveniently, the wash buffer and loading buffer may be the same, but this is not required.

The "elution buffer" is used to elute the polypeptide of interest from the solid phase. The conductivity and/or pH of the elution buffer is/are such that the polypeptide of interest is eluted from the ion exchange resin.

A "regeneration buffer" may be used to regenerate the ion exchange resin such that it can be re-used. The regeneration buffer has a conductivity and/or pH as required to remove substantially all impurities and the polypeptide of interest from the ion exchange resin.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially reduced," or "substantially different," as used herein with regard to amounts or numerical values (and not as reference to the chemical process of reduction), denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B.

It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

"Percent (%) nucleic acid sequence identity" is defined as the percentage of nucleotides in a candidate sequence that are identical with the nucleotides in a reference Factor D-encoding sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence identity is then calculated relative to the longer sequence, i.e. even if a shorter sequence shows 100% sequence identity with a portion of a longer sequence, the overall sequence identity will be less than 100%.

"Treatment" refers to both therapeutic treatment and prophylactic or preventative measures. Those in need of treatment include those already with the disorder as well as those in which the disorder is to be prevented. "Treatment" herein encompasses alleviation of the disease and of the signs and symptoms of the particular disease.

A "disorder" is any condition that would benefit from treatment with the protein. This includes chronic and acute disorders or diseases including those pathological conditions which predispose the mammal to the disorder in question. Non-limiting examples of disorders to be treated herein include carcinomas and allergies.

"Mammal" for purposes of treatment refers to any animal classified as a mammal, including humans, non-human higher primates, other vertebrates, domestic and farm animals, and zoo, sports, or pet animals, such as dogs, horses, cats, cows, etc. Preferably, the mammal is human.

B. Exemplary Methods and Materials for Carrying Out the Invention

The practice of the present invention will employ, unless otherwise indicated, conventional techniques of molecular biology and the like, which are within the skill of the art. Such techniques are explained fully in the literature. See e.g., *Molecular Cloning: A Laboratory Manual*, (J. Sambrook et al., Cold Spring Harbor Laboratory, Cold Spring Harbor, N.Y., 1989); *Current Protocols in Molecular Biology* (F. Ausubel et al., eds., 1987 updated); *Essential Molecular Biology* (T. Brown ed., IRL Press 1991); *Gene Expression Technology* (Goeddel ed., Academic Press 1991); *Methods for Cloning and Analysis of Eukaryotic Genes* (A. Bothwell et al., eds., Bartlett Publ. 1990); *Gene Transfer and Expression* (M. Kriegler, Stockton Press 1990); *Recombinant DNA Methodology II* (R. Wu et al., eds., Academic Press 1995); *PCR: A Practical Approach* (M. McPherson et al., IRL Press at Oxford University Press 1991); *Oligonucleotide Synthesis* (M. Gait ed., 1984); *Cell Culture for Biochemists* (R. Adams ed., Elsevier Science Publishers 1990); *Gene Transfer Vectors for Mammalian Cells* (J. Miller & M. Calos eds., 1987); *Mammalian Cell Biotechnology* (M. Butler ed., 1991); *Animal Cell Culture* (J. Pollard et al., eds., Humana Press 1990); *Culture of Animal Cells*, 2$^{nd}$ Ed. (R. Freshney et al., eds., Alan R. Liss 1987); *Flow Cytometry and Sorting* (M. Melamed et al., eds., Wiley-Liss 1990); the series *Methods in Enzymology* (Academic Press, Inc.); Wirth M. and Hauser H. (1993); *Immunochemistry in Practice*, 3rd edition, A. Johnstone & R. Thorpe, Blackwell Science, Cambridge, Mass., 1996; *Techniques in Immunocytochemistry*, (G. Bullock & P. Petrusz eds., Academic Press 1982, 1983, 1985, 1989); Handbook of Experimental Immunology, (D. Weir & C. Blackwell, eds.); *Current Protocols in Immunology* (J. Coligan et al., eds. 1991); *Immunoassay* (E. P. Diamandis & T. K. Christopoulos, eds., Academic Press, Inc., 1996); Goding (1986) *Monoclonal Antibodies: Principles and Practice* (2d ed) Academic Press, New York; Ed Harlow and David Lane, *Antibodies A laboratory Manual*, Cold Spring Harbor Laboratory, Cold Spring Harbor, N.Y., 1988; *Antibody Engineering*, 2$^{nd}$ edition (C. Borrebaeck, ed., Oxford University Press, 1995); and the series *Annual Review of Immunology*; the series *Advances in Immunology*.

1. Recombinant Production of Proteins in Mammalian Host Cells Using a Glutamine-Free Cell Culture Medium The present invention concerns the large-scale recombinant production of proteins in mammalian host cells, using a glutamine-free cell culture medium supplemented with asparagine. Mammalian cells have become the dominant system for the production of mammalian proteins for clinical applications, primarily due to their ability to produce properly folded and assembled heterologous proteins, and their capacity for post-translational modifications. Chinese hamster ovary (CHO) cells, and cell lines obtained from various other mammalian sources, such as, for example, mouse myeloma (NS0), baby hamster kidney (BHK), human embryonic kidney (HEK-293) and human retinal cells have been approved by regulatory agencies for the production of biopharmaceutical products, including therapeutic antibodies. Of these, Chinese Hamster Ovary Cells (CHO) are among the most commonly used industrial hosts, which are widely employed for the production of heterologous proteins. Thus, methods for the large-scale production of antibodies in CHO, including dihydrofolate reductase negative (DHFR−) CHO cells, are well known in the art (see, e.g. Trill et al., *Curr. Opin. Biotechnol.* 6(5):553-60 (1995) and U.S. Pat. No. 6,610,516).

As a first step, the nucleic acid (e.g., cDNA or genomic DNA) encoding the desired recombinant protein may be inserted into a replicable vector for cloning (amplification of the DNA) or for expression. Various vectors are publicly available. The vector components generally include, but are not limited to, one or more of the following: a signal sequence, an origin of replication, one or more marker genes, an enhancer element, a promoter, and a transcription termination sequence, each of which is described below. Optional signal sequences, origins of replication, marker genes, enhancer elements and transcription terminator sequences that may be employed are known in the art and described in further detail in PCT Publication WO 97/25428.

Expression and cloning vectors usually contain a promoter that is recognized by the host organism and is operably linked to the protein-encoding nucleic acid sequence. Promoters are untranslated sequences located upstream (5') to the start codon of a structural gene (generally within about 100 to 1000 bp) that control the transcription and translation of a particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to DNA encoding the desired protein by removing the promoter from the source DNA by restriction enzyme digestion and inserting the isolated promoter sequence into the vector.

Promoters suitable for use with prokaryotic and eukaryotic hosts are known in the art, and are described in further detail in PCT Publication No. WO97/25428.

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures can be used to transform *E. coli* cells, such as *E. coli* K12 strain 294 (ATCC® 31,446) and successful transformants selected by ampicillin or tetracycline resistance where appropriate. Plasmids from the transformants are prepared, analyzed by restriction endonuclease digestion, and/or sequenced using standard techniques known in the art. (See, e.g., Messing et al., *Nucleic Acids Res.* 1981, 9:309; Maxam et al., Methods in Enzymology 1980, 65:499).

Expression vectors that provide for the transient expression in mammalian cells may be employed. In general, transient expression involves the use of an expression vector that is able to replicate efficiently in a host cell, such that the host cell accumulates many copies of the expression vector and, in turn, synthesizes high levels of a desired polypeptide encoded by the expression vector (Sambrook et al., supra). Transient expression systems, comprising a suitable expression vector and a host cell, allow for the convenient positive identification of polypeptides encoded by cloned DNAs, as well as for the rapid screening of such polypeptides for desired biological or physiological properties.

Other methods, vectors, and host cells suitable for adaptation to the synthesis of a desired heterologous protein in recombinant vertebrate cell culture are described in Gething et al., *Nature* 1981, 293:620-625; Mantei et al., *Nature* 1979, 281:40-46; EP 117,060; and EP 117,058.

For large-scale production, according to the present invention mammalian host cells are transfected and preferably transformed with the above-described expression vectors and cultured in nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in Sambrook et al., supra, or electroporation is generally used for prokaryotes or other cells that contain substantial cell-wall barriers. Infection with Agrobacterium tumefaciens is used for transformation of certain plant cells, as described (Shaw et al., Gene 1983, 23:315 and PCT Publication No. WO 89/05859). In addition, plants may be transfected using ultrasound treatment, PCT Publication No. WO 91/00358 published 10 Jan. 1991.

For mammalian cells without such cell walls, the calcium phosphate precipitation method (Graham and van der Eb, *Virology* 1978, 52:456-457) may be employed. General aspects of mammalian cell host system transformations have been described in U.S. Pat. No. 4,399,216. For various techniques for transforming mammalian cells, see also Keown et al. *Methods in Enzymology* 1990, 185:527-537 and Mansour et al. *Nature* 1988, 336:348-352.

During large-scale production, to begin the production cycle usually a small number of transformed recombinant host cells is allowed to grow in culture for several days. Once the cells have undergone several rounds of replication, they are transferred to a larger container where they are prepared to undergo fermentation. The media in which the cells are grown and the levels of oxygen, nitrogen and carbon dioxide that exist during the production cycle may have a significant impact on the production process. Growth parameters are determined specifically for each cell line and these parameters are measured frequently to assure optimal growth and production conditions.

When the cells grow to sufficient numbers, they are transferred to large-scale production tanks to begin the production phase, and grown for a longer period of time. At this point in the process, the recombinant protein can be harvested. Typically, the cells are engineered to secrete the polypeptide into the cell culture media, so the first step in the purification process is to separate the cells from the media. Harvesting usually includes centrifugation and filtration to produce a Harvested Cell Culture Fluid (HCCF). The media is then subjected to several additional purification steps that remove any cellular debris, unwanted proteins, salts, minerals or other undesirable elements. At the end of the purification process, the recombinant protein is highly pure and is suitable for human therapeutic use.

Although this process has been the subject of much study and improvements over the past several decades, there is room fur further improvements in the large-scale commercial production of recombinant proteins, such as antibodies. Thus, increases in cell viability, longevity and specific productivity of mammalian host cell cultures, and improvements in the titer of the recombinant proteins produced have a genuine impact on the price of the recombinant protein produced, and, in the case of therapeutic proteins, the price and availability of drug products.

The present invention concerns an improved method for the production of heterologous proteins in mammalian cell culture, using a glutamine-free culture medium with added asparagine in the production phase of the cell culture process. The culture media used in the process of the present invention can be based on any commercially available medium for recombinant production of proteins in mammalian host cells, in particular CHO cells.

Examples of commercially available culture media include Ham's F10 (Sigma), Minimal Essential Medium ("MEM", Sigma), RPMI-1640 (Sigma), and Dulbecco's Modified Eagle's Medium ("DMEM", Sigma). Any such media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan. In addition, the culture media of the present invention can be based any of the media described in Ham and McKeehan, Meth. Enz., 58: 44 (1979); Barnes and Sato, Anal. Biochem., 102: 255 (1980); U.S. Pat. No. 4,767,704; U.S. Pat. No. 4,657,866; U.S. Pat. No. 4,927,762; U.S. Pat. No. 5,122,469 or U.S. Pat. No. 4,560,655; WO 90/03430; and WO 87/00195, provided that glutamine is omitted as an ingredient.

Under Glutamine-free conditions Asparagine is required since mammalian cells can synthesize Asparagine only in presence of Glutamine. Asparagine is synthesized by amide transfer from Glutamine in the presence of Asparagine synthetase. The Asparagine is preferably added to the culture medium at a concentration in the range of 2.5 mM to 15 mM. In various embodiments of the present invention, the preferred concentration of Asparagine should be at least 2.5 mM. In preferred embodiments, the asparagine is added at a concentration of 10 mM.

In general, principles, protocols, and practical techniques for maximizing the productivity of mammalian cell cultures can be found in, and can be adapted for the production of recombinant proteins using the cell culture media herein.

The necessary nutrients and growth factors for the medium, including their concentrations, for a particular cell line, are determined empirically without undue experimentation as described, for example, in *Mammalian Cell Culture*, Mather, ed. (Plenum Press: NY, 1984); Barnes and Sato, *Cell*, 22: 649 (1980) or *Mammalian Cell Biotechnology: A Practical Approach*, M. Butler, ed. (IRL Press, 1991). A suitable medium contains a basal medium component such as a DMEM/HAM F-12-based formulation (for composition of DMEM and HAM F12 media and especially serum-free media, see culture media formulations in American Type Culture Collection Catalogue of Cell Lines and Hybridomas, Sixth Edition, 1988, pages 346-349), with modified concentrations of some components such as amino acids, salts, sugar, and vitamins, and optionally containing glycine, hypoxanthine, and thymidine; recombinant human insulin, hydrolyzed peptone, such as PRIMATONE HS™ or PRIMATONE RL™ (Sheffield, England), or the equivalent; a cell protective agent, such as PLURONIC F68™ or the equivalent pluronic polyol; GENTAMYCIN™; and trace elements. The formulations of medium as described in U.S. Pat. No. 5,122,469, characterized by the presence of high levels of certain amino acids, as well as PS-20 as described below, are particularly appropriate.

The glycoproteins of the present invention may be produced by growing cells which express the desired glycoprotein under a variety of cell culture conditions. For instance, cell culture procedures for the large- or small-scale production of glycoproteins are potentially useful within the context of the present invention. Procedures including, but not limited to, a fluidized bed bioreactor, hollow fiber bioreactor, roller bottle culture, or stirred tank bioreactor system may be used, in the later two systems, with or without microcarriers, and operated alternatively in a batch, fed-batch, or continuous mode.

In a particular embodiment the cell culture of the present invention is performed in a stirred tank bioreactor system and a fed-batch culture procedure is employed. In the preferred fed-batch culture the mammalian host cells and culture medium are supplied to a culturing vessel initially and additional culture nutrients are fed, continuously or in discrete increments, to the culture during culturing, with or without periodic cell and/or product harvest before termination of culture. The fed-batch culture can include, for example, a semi-continuous fed-batch culture, wherein periodically whole culture (including cells and medium) is removed and replaced by fresh medium Fed-batch culture is distinguished from simple-batch culture in which all components for cell culturing (including the cells and all culture nutrients) are supplied to the culturing vessel at the start of the culturing process. Fed-batch culture can be further distinguished from perfusion culturing insofar as the supernate is not removed from the culturing vessel during the process (in perfusion culturing, the cells are restrained in the culture by, e.g., filtration, encapsulation, anchoring to microcarriers, etc., and the culture medium is continuously or intermittently introduced and removed from the culturing vessel).

Further, the cells of the culture may be propagated according to any scheme or routine that may be suitable for the particular host cell and the particular production plan contemplated. Therefore, the present invention contemplates a single-step or multiple-step culture procedure. In a single-step culture the host cells are inoculated into a culture environment and the processes of the instant invention are employed during a single production phase of the cell culture. Alternatively, a multi-stage culture is envisioned. In the multi-stage culture cells may be cultivated in a number of steps or phases. For instance, cells may be grown in a first step or growth phase culture wherein cells, possibly removed from storage, are inoculated into a medium suitable for promoting growth and high viability. The cells may be maintained in the growth phase for a suitable period of time by the addition of fresh medium to the host cell culture.

According to a specific aspect of the invention, fed-batch or continuous cell culture conditions are devised to enhance growth of the mammalian cells in the growth phase of the cell culture. In the growth phase cells are grown under conditions and for a period of time that is maximized for growth. Culture conditions, such as temperature, pH, dissolved oxygen ($DO_2$), and the like, are those used with the particular host and will be apparent to the ordinarily-skilled artisan. Generally, the pH is adjusted to a level between about 6.5 and 7.5 using either an acid (e.g., $CO_2$) or a base (e.g., $Na_2CO_3$ or NaOH). A suitable temperature range for culturing mammalian cells such as CHO cells is between about 30 to 40° C. and preferably about 37° C. and a suitable $DO_2$ is between 5-90% of air saturation.

At a particular stage the cells may be used to inoculate a production phase or step of the cell culture. Alternatively, as described above the production phase or step may be continuous with the inoculation or growth phase or step.

Production of a target protein in mammalian, e.g., CHO, cells typically employs a semi-continuous process whereby cells are culture in a "seed-train" for various periods of time and are periodically transferred to inoculum fermentors to generate enough cell mass to inoculate a production fermentor at larger scale. Thus, cells used for the production of the desired protein are in culture for various periods of time up to a maximum predefined cell age. The parameters of the cell culture process, such as seed density, pH, $DO_2$ and temperature during culture, duration of the production culture, operating conditions of harvest, etc. are a function of the particular cell line and culture medium used, and can be determined empirically, without undue experimentation.

According to the present invention, the cell-culture environment during the production phase of the cell culture is controlled. In a preferred aspect, the production phase of the cell culture process is preceded by a transition phase of the cell culture in which parameters for the production phase of the cell culture are engaged.

The desired polypeptide, such as antibody, preferably is recovered from the culture medium as a secreted polypeptide, although it also may be recovered from host cell lysates when directly produced without a secretory signal. If the polypeptide is membrane-bound, it can be released from the membrane using a suitable detergent solution (e.g., Triton-X 100) or its extracellular region may be released by enzymatic cleavage.

When the polypeptide is produced in a recombinant cell other than one of human origin, it is free of proteins or polypeptides of human origin. However, it is usually necessary to recover or purify recombinant proteins from recombinant cell proteins or polypeptides to obtain preparations that are substantially homogeneous as to the desired polypeptide. As a first step, the culture medium or lysate may be centrifuged to remove particulate cell debris. The heterologous polypeptide thereafter is purified from contaminant soluble proteins and polypeptides, with the following procedures being exemplary of suitable purification procedures: by fractionation on an ion-exchange column such as SP-Sepharose™ or CM-Sepharose™; hydroxyapatite; hydrophobic interaction chromatography; ethanol precipitation;

chromatofocusing; ammonium sulfate precipitation; gel filtration using, for example, Sephadex G-75™; and/or diafiltration.

Recombinant polypeptides can be isolated, e.g. by affinity chromatography.

A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for the purification and isolation of recombinant proteins, including antibodies, can be used herein, and modified if needed, using standard techniques.

Expression of the desired heterologous protein may be measured in a sample directly, for example, by conventional Southern blotting, Northern blotting to quantitate the transcription of mRNA (Thomas, *Proc. Natl. Acad. Sci. USA* 1980, 77:5201-5205), dot blotting (DNA analysis), or in situ hybridization, using an appropriately labeled probe, based on the sequences provided herein. Various labels may be employed, most commonly radioisotopes, and particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionucleotides, fluorescers or enzymes. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. Antibodies useful for immunohistochemical staining and/or assay of sample fluids may be either monoclonal or polyclonal, and may be prepared in any mammal 2. Antibodies In a preferred embodiment, the methods of the present invention are used for the recombinant production of antibodies, including therapeutic and diagnostic antibodies. Antibodies within the scope of the present invention include, but are not limited to: anti-HER2 antibodies including Trastuzumab (HERCEPTIN®) (Carter et al., *Proc. Natl. Acad. Sci. USA,* 89:4285-4289 (1992), U.S. Pat. No. 5,725,856); anti-CD20 antibodies such as chimeric anti-CD20 "C2B8" as in U.S. Pat. No. 5,736,137 (RITUXAN®), a chimeric or humanized variant of the 2H7 antibody as in U.S. Pat. No. 5,721,108B1, or Tositumomab (BEXXAR®); anti-IL-8 (St John et al., *Chest,* 103:932 (1993), and International Publication No. WO 95/23865); anti-VEGF antibodies including humanized and/or affinity matured anti-VEGF antibodies such as the humanized anti-VEGF antibody huA4.6.1 AVASTIN® (Kim et al., *Growth Factors,* 7:53-64 (1992), International Publication No. WO 96/30046, and WO 98/45331, published Oct. 15, 1998); anti-PSCA antibodies (WO01/40309); anti-CD40 antibodies, including S2C6 and humanized variants thereof (WO00/75348); anti-CD11a (U.S. Pat. No. 5,622,700, WO 98/23761, Steppe et al., *Transplant Intl.* 4:3-7 (1991), and Hourmant et al., *Transplantation* 58:377-380 (1994)); anti-IgE (Presta et al., *J. Immunol.* 151:2623-2632 (1993), and International Publication No. WO 95/19181); anti-CD18 (U.S. Pat. No. 5,622,700, issued Apr. 22, 1997, or as in WO 97/26912, published Jul. 31, 1997); anti-IgE (including E25, E26 and E27; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714, 338); anti-Apo-2 receptor antibody (WO 98/51793 published Nov. 19, 1998); anti-TNF-α antibodies including cA2 (REMICADE®), CDP571 and MAK-195 (See, U.S. Pat. No. 5,672,347 issued Sep. 30, 1997, Lorenz et al., *J. Immunol.* 156(4):1646-1653 (1996), and Dhainaut et al., *Crit. Care Med.* 23(9):1461-1469 (1995)); anti-Tissue Factor (TF) (European Patent No. 0 420 937 B1 granted Nov. 9, 1994); anti-human $α_4β_7$ integrin (WO 98/06248 published Feb. 19, 1998); anti-EGFR (chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-tac antibodies such as CHI-621 (SIMULECT®) and (ZENAPAX®) (See U.S. Pat. No. 5,693, 762 issued Dec. 2, 1997); anti-CD4 antibodies such as the cM-7412 antibody (Choy et al., *Arthritis Rheum* 39(1):52-56 (1996)); anti-CD52 antibodies such as CAMPATH-1H (Riechmann et al., *Nature* 332:323-337 (1988)); anti-Fc receptor antibodies such as the M22 antibody directed against FcγRI as in Graziano et al., *J. Immunol.* 155(10):4996-5002 (1995); anti-carcinoembryonic antigen (CEA) antibodies such as hMN-14 (Sharkey et al., *Cancer Res.* 55(23Suppl): 5935s-5945s (1995); antibodies directed against breast epithelial cells including huBrE-3, hu-Mc 3 and CHL6 (Ceriani et al., *Cancer Res.* 55(23): 5852s-5856s (1995); and Richman et al., *Cancer Res.* 55(23 Supp): 5916s-5920s (1995)); antibodies that bind to colon carcinoma cells such as C242 (Litton et al., *Eur J. Immunol.* 26(1):1-9 (1996)); anti-CD38 antibodies, e.g. AT 13/5 (Ellis et al., *J. Immunol.* 155(2):925-937 (1995)); anti-CD33 antibodies such as Hu M195 (Jurcic et al., *Cancer Res* 55(23 Suppl):5908s-5910s (1995) and CMA-676 or CDP771; anti-CD22 antibodies such as LL2 or Lympho- Cide (Juweid et al., *Cancer Res* 55(23 Suppl):5899s-5907s (1995)); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIR®; anti-CA 125 antibody OvaRex; anti-idiotypic GD3 epitope antibody BEC2; anti-αvβ3 antibody VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1). The preferred target antigens for the antibody herein are: HER2 receptor, VEGF, IgE, CD20, CD11a, and CD40.

Many of these antibodies are widely used in clinical practice to treat various diseases, including cancer.

In certain specific embodiments, the methods of the present invention are used for the production of the following antibodies and recombinant proteins.

Anti-CD20 Antibodies

Rituximab (RITUXAN®) is a genetically engineered chimeric murine/human monoclonal antibody directed against the CD20 antigen. Rituximab is the antibody called "C2B8" in U.S. Pat. No. 5,736,137 issued Apr. 7, 1998 (Anderson et al.). Rituximab is indicated for the treatment of patients with relapsed or refractory low-grade or follicular, CD20-positive, B cell non-Hodgkin's lymphoma. In vitro mechanism of action studies have demonstrated that rituximab binds human complement and lyses lymphoid B cell lines through complement-dependent cytotoxicity (CDC) (Reff et al., *Blood* 83(2): 435-445 (1994)). Additionally, it has significant activity in assays for antibody-dependent cellular cytotoxicity (ADCC). More recently, rituximab has been shown to have anti-proliferative effects in tritiated thymidine incorporation assays and to induce apoptosis directly, while other anti-CD19 and CD20 antibodies do not (Maloney et al., *Blood* 88(10):637a (1996)). Synergy between rituximab and chemotherapies and toxins has also been observed experimentally. In particular, rituximab. sensitizes drug-resistant human B cell lymphoma cell lines to the cytotoxic effects of doxorubicin, CDDP, VP-1 6, diphtheria toxin and ricin (Demidem et al., *Cancer Chemotherapy & Radiopharmaceuticals* 12(3):177-186 (1997)). In vivo preclinical studies have shown that rituximab depletes B cells from the peripheral blood, lymph nodes, and bone marrow of cynomolgus monkeys, presumably through complement and cell-mediated processes (Reff et al., *Blood* 83(2): 435-445 (1994)).

Patents and patent publications concerning CD20 antibodies include U.S. Pat. Nos. 5,776,456, 5,736,137, 6,399,061, and 5,843,439, as well as U.S. patent application Nos. US 2002/0197255A1, US 2003/0021781A1, US 2003/0082172 A1, US 2003/0095963 A1, US 2003/0147885 A1 (Anderson et al.); U.S. Pat. No. 6,455,043B1 and WO00/09160 (Grillo-Lopez, A.); WO00/27428 (Grillo-Lopez and White); WO00/27433 (Grillo-Lopez and Leonard); WO00/44788 (Braslawsky et al.); WO01/10462 (Rastetter, W.); WO01/10461 (Rastetter and White); WO01/10460 (White and Grillo-Lopez); U.S. application No. US2002/0006404 and WO02/04021 (Hanna and Hariharan); U.S. application No. US2002/0012665 A1 and WO01/74388 (Hanna, N.); U.S. application No. US 2002/0058029 A1 (Hanna, N.); U.S. application No. US 2003/0103971 A1 (Hariharan and Hanna); U.S. application No. US2002/0009444A1, and WO01/80884 (Grillo-Lopez, A.); WO01/97858 (White, C.); U.S. application No. US2002/0128488A1 and WO02/34790 (Reff, M.); W)02/060955 (Braslawsky et al.); WO2/096948 (Braslawsky et al.); WO02/079255 (Reff and Davies); U.S. Pat. No. 6,171,586B1, and WO98/56418 (Lam et al.); WO98/58964 (Raju, S.); WO99/22764 (Raju, S.); WO99/51642, U.S. Pat. No. 6,194,551B1, U.S. Pat. No. 6,242,195B1, U.S. Pat. No. 6,528,624B1 and U.S. Pat. No. 6,538,124 (Idusogie et al.); WO00/42072 (Presta, L.); WO00/67796 (Curd et al.); WO01/03734 (Grillo-Lopez et al.); U.S. application No. US 2002/0004587A1 and WO01/77342 (Miller and Presta); U.S. application No. US2002/0197256 (Grewal, I.); U.S. application No. US 2003/0157108 A1 (Presta, L.); U.S. Pat. Nos. 6,090,365B1, 6,287,537B1, 6,015,542, 5,843,398, and 5,595,721, (Kaminski et al.); U.S. Pat. Nos. 5,500,362, 5,677, 180, 5,721,108, and 6,120,767 (Robinson et al.); U.S. Pat. No. 6,410,391B1 (Raubitschek et al.); U.S. Pat. No. 6,224, 866B1 and WO00/20864 (Barbera-Guillem, E.); WO01/13945 (Barbera-Guillem, E.); WO00/67795 (Goldenberg); U.S. application No. US 2003/01339301 A1 and WO00/74718 (Goldenberg and Hansen); WO00/76542 (Golay et al.); WO01/72333 (Wolin and Rosenblatt); U.S. Pat. No. 6,368,596B1 (Ghetie et al.); U.S. application No. US2002/0041847 A1, (Goldenberg, D.); U.S. application No. US2003/0026801A1 (Weiner and Hartmann); WO02/102312 (Engleman, E.); U.S. patent application No. 2003/0068664 (Albitar et al.); WO03/002607 (Leung, S.); WO 03/049694 and US 2003/0185796 A1 (Wolin et al.); WO03/061694 (Sing and Siegall); US 2003/0219818 A1 (Bohen et al.); US 2003/0219433 A1 and WO 03/068821 (Hansen et al.) each of which is expressly incorporated herein by reference. See, also, U.S. Pat. No. 5,849,898 and EP application no. 330,191 (Seed et al.); U.S. Pat. No. 4,861,579 and EP332, 865A2 (Meyer and Weiss); U.S. Pat. No. 4,861,579 (Meyer et al.) and WO95/03770 (Bhat et al.).

Publications concerning therapy with Rituximab include: Perotta and Abuel "Response of chronic relapsing ITP of 10 years duration to Rituximab" Abstract #3360 *Blood* 10(1) (part 1-2): p. 88B (1998); Stashi et al., "Rituximab chimeric anti-CD20 monoclonal antibody treatment for adults with chronic idopathic thrombocytopenic purpura" *Blood* 98(4): 952-957 (2001); Matthews, R. "Medical Heretics" New Scientist (7 Apr. 2001); Leandro et al., "Clinical outcome in 22 patients with rheumatoid arthritis treated with B lymphocyte depletion" *Ann Rheum Dis* 61:833-888 (2002); Leandro et al., "Lymphocyte depletion in rheumatoid arthritis: early evidence for safety, efficacy and dose response. *Arthritis & Rheumatism* 44(9): 5370 (2001); Leandro et al., "An open study of B lymphocyte depletion in systemic lupus erythematosus", *Arthritis & Rheumatism* 46(1):2673-2677 (2002); Edwards and Cambridge "Sustained improvement in rheumatoid arthritis following a protocol designed to deplete B lymphocytes" *Rheumatology* 40:205-211 (2001); Edwards et al., "B-lymphocyte depletion therapy in rheumatoid arthritis and other autoimmune disorders" *Biochem. Soc. Trans.* 30(4):824-828 (2002); Edwards et al., "Efficacy and safety of Rituximab, a B-cell targeted chimeric monoclonal antibody: A randomized, placebo controlled trial in patients with rheumatoid arthritis. *Arthritis & Rheumatism* 46(9): 5197 (2002); Levine and Pestronk "IgM antibody-related polyneuropathies: B-cell depletion chemotherapy using Rituximab" *Neurology* 52: 1701-1704 (1999); DeVita et al., "Efficacy of selective B cell blockade in the treatment of rheumatoid arthritis" *Arthritis & Rheumatism* 46:2029-2033 (2002); Hidashida et al., "Treatment of DMARD-Refractory rheumatoid arthritis with rituximab." Presented at the Annual Scientific Meeting of the American College of Rheumatology;

October 24-29; New Orleans, La. 2002; Tuscano, J. "Successful treatment of Infliximab-refractory rheumatoid arthritis with rituximab" Presented at the Annual Scientific Meeting of the American College of Rheumatology; October 24-29; New Orleans, La. 2002. Sarwal et al., *N. Eng. J. Med.* 349(2):125-138 (Jul. 10, 2003) reports molecular heterogeneity in acute renal allograft rejection identified by DNA microarray profiling.

In various embodiments, the invention provides pharmaceutical compositions comprising humanized anti-CD20 antibodies. In certain embodiments, the humanized antibody composition of the invention further comprises amino acid alterations in the IgG Fc and exhibits increased binding affinity for human FcRn over an antibody having wild-type IgG Fc, by at least 60 fold, at least 70 fold, at least 80 fold, more preferably at least 100 fold, preferably at least 125 fold, even more preferably at least 150 fold to about 170 fold.

The N-glycosylation site in IgG is at Asn297 in the $C_H2$ domain. Humanized antibody compositions of the present invention include compositions of any of the preceding humanized antibodies having an Fc region, wherein about 80-100% (and preferably about 90-99%) of the antibody in the composition comprises a mature core carbohydrate structure which lacks fucose, attached to the Fc region of the glycoprotein. Such compositions were demonstrated herein to exhibit a surprising improvement in binding to Fc(RIIIA (F158), which is not as effective as Fc(RIIIA (V158) in interacting with human IgG. Fc(RIIIA (F158) is more common than Fc(RIIIA (V 158) in normal, healthy African Americans and Caucasians. See Lehrnbecher et al., *Blood* 94:4220 (1999). Historically, antibodies produced in Chinese Hamster Ovary Cells (CHO), one of the most commonly used industrial hosts, contain about 2 to 6% in the population that are nonfucosylated. YB2/0 and Lec13, however, can produce antibodies with 78 to 98% nonfucosylated species. Shinkawa et al., *J Bio. Chem.* 278 (5), 3466-347 (2003), reported that antibodies produced in YB2/0 and Lec13 cells, which have less FUT8 activity, show significantly increased ADCC activity in vitro. The production of antibodies with reduced fucose content are also described in e.g., Li et al., (GlycoFi) "Optimization of humanized IgGs in glycoengineered *Pichia pastoris*" in Nature Biology online publication 22 Jan. 2006; Niwa R. et al., *Cancer Res.* 64(6):2127-2133 (2004); US 2003/0157108 (Presta); U.S. Pat. No. 6,602,684 and US 2003/0175884 (Glycart Biotechnology); US 2004/0093621, US 2004/0110704, US 2004/0132140 (all of Kyowa Hakko Kogyo).

A bispecific humanized antibody encompasses an antibody wherein one arm of the antibody has at least the antigen binding region of the H and/or L chain of a humanized antibody of the invention, and the other arm has V region binding specificity for a second antigen. In specific embodiments, the antigens are selected from the group consisting of CD-20, CD3, CD64, CD32A, CD16, NKG2D or other NK activating ligands.

Anti-HER2 Antibodies

A recombinant humanized version of the murine HER2 antibody 4D5 (huMAb4D5-8, rhuMAb HER2, trastuzumab or HERCEPTIN®; U.S. Pat. No. 5,821,337) is clinically active in patients with HER2-overexpressing metastatic breast cancers that have received extensive prior anti-cancer therapy (Baselga et al., *J. Clin. Oncol.* 14:737-744 (1996)). Trastuzumab received marketing approval from the Food and Drug Administration (FDA) Sep. 25, 1998 for the treatment of patients with metastatic breast cancer whose tumors over-express the HER2 protein. In November 2006, the FDA approved Herceptin as part of a treatment regimen containing doxorubicin, cyclophosphamide and paclitaxel, for the adjuvant treatment of patients with HER2-positive, node-positive breast cancer.

In various embodiments, the invention provides pharmaceutical compositions comprising humanized anti-HER2 antibodies. HER2 antibodies with various properties have been described in Tagliabue et al., *Int. J. Cancer* 47:933-937 (1991); McKenzie et al., *Oncogene* 4:543-548 (1989); Maier et al., *Cancer Res.* 51:5361-5369 (1991); Bacus et al., *Molecular Carcinogenesis* 3:350-362 (1990); Stancovski et al., *PNAS (USA)* 88:8691-8695 (1991); Bacus et al., *Cancer Research* 52:2580-2589 (1992); Xu et al., *Int. J. Cancer* 53:401-408 (1993); WO94/00136; Kasprzyk et al., *Cancer Research* 52:2771-2776 (1992); Hancock et al., *Cancer Res.* 51:4575-4580 (1991); Shawver et al., *Cancer Res.* 54:1367-1373 (1994); Arteaga et al., *Cancer Res.* 54:3758-3765 (1994); Harwerth et al., *J. Biol. Chem.* 267:15160-15167 (1992); U.S. Pat. No. 5,783,186; and Klapper et al., *Oncogene* 14:2099-2109 (1997).

Anti-VEGF Antibodies anti-VEGF antibodies including humanized and/or affinity matured anti-VEGF antibodies such as the humanized anti-VEGF antibody huA4.6.1 AVASTIN® (Kim et al., *Growth Factors,* 7:53-64 (1992), International Publication No. WO 96/30046, and WO 98/45331, published Oct. 15, 1998) are FDA approved for the treatment of cancer. In various embodiments, the invention provides pharmaceutical compositions comprising humanized anti-VEGF antibodies.

Anti-CD11a Antibodies

The humanized anti-CD11a antibody efalizumab or Raptiva (U.S. Pat. No. 6,037,454) received marketing approval from the Food and Drug Administration on Oct. 27, 2003 for the treatment for the treatment of psoriasis. One embodiment provides for pharmaceutical compositions comprising anti-human CD11a antibodies.

Apomab Antibodies

Antibodies to the DR5 receptor (anti-DR5) antibodies can also be produced in accordance with the present invention. Such anti-DR5 antibodies specifically include all antibody variants disclosed in PCT Publication No. WO 2006/083971, such as the anti-DR5 antibodies designated Apomabs 1.1, 2.1, 3.1, 4.1, 5.1, 5.2, 5.3, 6.1, 6.2, 6.3, 7.1, 7.2, 7.3, 8.1, 8.3, 9.1, 1.2, 2.2, 3.2, 4.2, 5.2, 6.2, 7.2, 8.2, 9.2, 1.3, 2.3, 3.3, 4.3, 5.3, 6.3, 7.3, 8.3, 9.3, and 25.3, especially Apomab 8.3 and Apomab 7.3, preferably Apomab 7.3. The entire content of WO 2006/083971 is hereby expressly incorporated by reference. Apomab is a fully human monoclonal antibody which is a DR5-targeted pro-apoptotic receptor agonist (PARA) specifically designed to induce apoptosis. Apoptosis is a natural process by which damaged or unwanted cells, including those that are cancerous, die and are cleared from the body. Pro-apoptotic receptor DR5 is expressed in a broad range of malignancies.

Anti-BR3 Antibodies and Immunoadhesins

Antibodies to the BR3 (anti-BR3) antibodies and BR3-Fc immunoadhesins can also be produced in accordance with the present invention. Such anti-BR3 antibodies and immunoadhesins specifically include all variants disclosed in U.S. Application Publication No. 20050070689. The entire content of U.S. Application Publication No. 20050070689 is hereby expressly incorporated by reference.

3. General Methods for the Recombinant Production of Antibodies

The antibodies and other recombinant proteins herein can be produced by well known techniques of recombinant DNA technology. Thus, aside from the antibodies specifically identified above, the skilled practitioner could generate antibodies directed against an antigen of interest, e.g., using the techniques described below.

Antigen Selection and Preparation

The antibody herein is directed against an antigen of interest. Preferably, the antigen is a biologically important polypeptide and administration of the antibody to a mammal suffering from a disease or disorder can result in a therapeutic benefit in that mammal However, antibodies directed against nonpolypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those proteins described in section (3) below. Exemplary molecular targets for antibodies encompassed by the present invention include CD proteins such as CD3, CD4, CD8, CD19, CD20, CD22, CD34, CD40; members of the ErbB receptor family such as the EGF receptor, HER2, HER3 or HER4 receptor; cell adhesion molecules such as LFA-1, Mac1, p150,95, VLA-4, ICAM-1, VCAM and $\alpha v/\beta 3$ integrin including either $\alpha$ or $\beta$ subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C, or any of the other antigens mentioned herein. Antigens to which the antibodies listed above bind are specifically included within the scope herein.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

Other antigens and forms thereof useful for preparing antibodies will be apparent to those in the art.

Polyclonal Antibodies

Polyclonal antibodies are preferably raised in animals by multiple subcutaneous (sc) or intraperitoneal (ip) injections of the relevant antigen and an adjuvant. It may be useful to conjugate the antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of antigen or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, Protein A-Sepharose, hydroxyapatite chromatography, gel electrophoresis, dialysis, or affinity chromatography. Preferably the Protein A chromatography procedure described herein is used.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In a further embodiment, monoclonal antibodies can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.,* 21:2265-2266 (1993)). Thus, these techniques are viable alternatives to traditional hybridoma techniques for isolation of monoclonal antibodies.

Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239: 1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (Sims et al., *J. Immunol.,* 151:2296 (1993)). Another method uses a particular framework derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immnol.,* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); and Duchosal et al., *Nature* 355:258 (1992). Human antibodies can also be derived from phage-display libraries (Hoogenboom et al., *J. Mol. Biol.,* 227:381 (1991); Marks et al., *J Mol. Biol.,* 222:581-597 (1991); Vaughan et al., *Nature Biotech* 14:309 (1996)).

Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science,* 229: 81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., Bio/Technology 10:163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv) (see WO 93/16185).

Multispecific Antibodies

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein.

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994). Alternatively, the antibodies can be "linear antibodies" as described in Zapata et al., Protein Eng. 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

Antibodies with more than two valencies are contemplated. For example, trispecific antibodies can be prepared. Tutt et al., J. Immunol. 147: 60 (1991).

Immunoadhesins

The simplest and most straightforward immunoadhesin design combines the binding domain(s) of the adhesin (e.g. the extracellular domain (ECD) of a receptor) with the hinge and Fc regions of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the immunoadhesin.

In a preferred embodiment, the adhesin sequence is fused to the N-terminus of the Fc domain of immunoglobulin G$_1$ (IgG$_1$). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagrammed below:

$AC_L$-$AC_L$;
$AC_H$-($AC_H$, $AC_L$-$AC_H$, $AC_L$-$V_H C_H$, or $V_L C_L$-$AC_H$);
$AC_L$-$AC_H$-($AC_L$-$AC_H$, $AC_L$-$V_H C_H$, $V_L C_L$-$AC_H$, or $V_L C_L$-$V_H C_H$)
$AC_L$-$V_H C_H$-($AC_H$, or $AC_L$-$V_H C_H$, or $V_L C_L$-$AC_H$);
$V_L C_L$-$AC_H$-($AC_L$-$V_H C_H$, or $V_L C_L$-$AC_H$); and
$(A$-$Y)_n$-$(V_L C_L$-$V_H C_H)_2$;

wherein each A represents identical or different adhesin amino acid sequences;

$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown.

However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H 2$ domain, or between the $C_H 2$ and $C_H 3$ domains. Similar constructs have been reported by Hoogenboom, et al., *Mol. Immunol.* 28:1027-1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g. Aruffo et al., *Cell* 61:1303-1313 (1990); and Stamenkovic et al., *Cell* 66:1133-1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

Further details of the invention are provided in the following non-limiting Examples.

All patents, patent applications, publications, product descriptions, and protocols are cited throughout this application, the disclosures of which are incorporated herein by reference in their entireties.

EXAMPLES

The following examples are offered for illustrative purposes only, and are not intended to limit the scope of the present invention in any way. Commercially available reagents referred to in the examples were used according to manufacturer's instructions unless otherwise indicated. The source of those cells identified in the following examples, and throughout the specification, by ATCC® accession numbers is the American Type Culture Collection, Manassas, Va.

Example 1

Production of Polypeptides in Glutamine-Free Production Medium

Materials and Methods:
Cell Lines.

In these studies, CHO host cells expressing an Apomab antibody, anti-VEGF antibody, and the fusion protein BR3-Fc, respectively were used. The host cells were adapted in suspension and serum free cultures. Frozen stocks were prepared as master or working cell banks in the media described below.

Cell line maintenance was carried out using a 250-mL or 1-Liter Corning® vented shake flasks maintained in a Thermo Scientific Forma® reach-in a $CO_2$ humidified incubator maintained at 37° C. and 5% $CO_2$. Flasks were agitated at rate of 150 rpm on a New Brunswick Scientific Innova®-2100 platform shaker with a custom aluminum-substrate platform. Cell cultures were passed every 3 or 4 days with fresh media and seeded at 0.11% or 0.20% Packed Cell Volume (PCV). PCV was obtained using a glass 10-mL KIMAX® USA PCV tube.

Culture Media and Conditions.

Media studies were initiated using 250-mL Corning vented shake flask inoculated in singlet, duplicate, or triplicate at 100 mL working volume at 0.20% PCV for all cases using cell culture from a source 1-Liter Corning® vented shake flask with a 500-mL working volume. PCV was obtained using a glass 10-mL KIMAX® USA PCV tube.

Prior to initiation of the study cell culture was centrifuged at 1000 rpm for 5-minutes in a Sorvall® RT 6000B centrifuge to complete a 100% media exchange of inoculum media containing glutamine with the respective test media. Different concentrations of Glutamine, Glutamate, Asparagine and Aspartate were evaluated in the different test media. The following concentrations were tested: Glutamine 0-10 mM, Glutamate 1-10 mM, Asparagine 0-15 mM, Aspartate 1-10 mM. Media conditions were evaluated in full factorial DOE studies.

The effect of Glutamine-free medium on was also tested in commercially available DMEM/F12 medium. The medium was used at 5× concentration (7.05 g/L) with extra Asparagine (10 mM total), Aspartate (10 mM total), Glutamine (10 mM total for the Glutamine-containing medium), Glutamate (1 mM total), and glucose (8 g/L total). Glutamine-free and Glutamine-containing medium were compared using Apomab and anti-VEGF antibody expressing cells.

Shake flasks were maintained in a Thermo Scientific Forma® reach-in a $CO_2$ humidified incubator maintained at 37° C. and 5% $CO_2$. Flasks were agitated at rate of 150 rpm on a New Brunswick Scientific Innova®-2100 platform shaker with a custom aluminum-substrate platform.

The medium used contained the following components:
Organic Salts and Trace Elements
Ammonium Paramolybdate, Tetrahydrate
Ammonium Vanadium Oxide
Calcium Chloride, Anhydrous
Cupric Sulfate, Pentahydrate
Ferrous Sulfate, Heptahydrate
Potassium Chloride
Magnesium Chloride, Anhydrous
Manganese Sulfate, Monohydrate
Nickel Chloride, Hexahydrate
Selenious Acid
Sodium Metasilicate, Nonahydrate
Sodium Phosphate, Monobasic, Monohydrate
Stannous Chloride, Dihydrate
Zinc Sulfate, Heptahydrate
Lipids
Linoleic Acid
Lipoic Acid (aka Thioctic Acid)
Putrescine, Dihydrochloride
Amino Acids
L-Alanine
L-Arginine, Monohydrochloride
L-Asparagine
L-Aspartic Acid
L-Cysteine, Monohydrochloride, Monohydrate
L-Glutamic Acid
L-Glutamine
L-Histidine, Monohydrochloride, Monohydrate
L-Isoleucine
L-Leucine
L-Lysine, Monohydrochloride
L-Methionine
L-Phenylalanine
L-Proline
L-Serine
L-Threonine
L-Tryptophan
L-Tyrosine, Disodium Salt, Dihydrate
L-Valine
Vitamins
Biotin
D-Calcium Pantothenate
Choline Chloride
Folic Acid
I-Inositol
Niacinamide
Pyridoxine, Monohydrochloride
Riboflavin
Thiamine, Monohydrochloride
Vitamin B-12
Carbon Source, Growth Factors, and Miscellaneous
Fluronic F-68
D-Glucose
Sodium Bicarbonate
Sodium Pyruvate
Sodium Chloride
Sodium Hydroxide
Insulin
Galactose The commercially-available DMEM/F-12 culture medium was also tested, having the following components;

|  | (mg/L) |
|---|---|
| VITAMINS | |
| Biotin | 0.00365 |
| D-calcium pantothenate | 2.24 |
| Choline chloride | 8.98 |
| Cyanocobalamin | 0.68 |
| Folic acid | 2.65 |
| i-inositol | 12.6 |
| Niacinamide | 2.0185 |
| Pyridoxal HCl | 2 |
| Pyridoxine HCl | 0.031 |
| Riboflavin | 0.219 |
| Thiamine HCl | 2.17 |
| AMINO ACIDS | |
| L-alanine | 4.455 |
| L-arginine HCl | 147.5 |
| L-asparagine monohydrate | 7.5 |
| L-aspartic acid | 6.65 |
| L-cysteine HCl monohydrate | 17.56 |
| L-cystine 2HCl | 31.29 |
| L-glutamic acid | 7.35 |
| L-glutamine | 365 |
| Glycine | 18.75 |
| L-histidine HCl monohydrate | 31.48 |
| L-isoleucine | 54.47 |
| L-leucine | 59.05 |
| L-lysine HCl | 91.25 |
| L-methionine | 17.24 |
| L-phenylalanine | 35.48 |
| L-proline | 17.25 |
| L-serine | 26.25 |
| L-threonine | 53.45 |
| L-tryptophan | 9.02 |
| L-tyrosine 2Na dihydrate | 55.79 |
| L-valine | 52.85 |
| OTHER | |
| Dextrose anhydrous | 3151 |
| HEPES | 3575 |
| Hypoxanthine sodium salt | 2.39 |
| Linoleic acid | 0.042 |
| DL-α-Lipoic acid | 0.105 |
| Phenol red sodium salt | 8.602 |
| Putrescine 2HCl | 0.081 |
| Sodium pyruvate | 55 |
| Thymidine | 0.365 |
| ADD: Sodium bicarbonate | 1200 |
| INORGANIC SALTS | |
| Calcium chloride anhydrous | 116.61 |
| Cupric sulfate pentahydrate | 0.00125 |
| Ferric nitrate nonahydrate | 0.05 |
| Ferrous sulfate heptahydrate | 0.417 |
| Magnesium chloride anhydrous | 28.61 |
| Magnesium sulfate anhydrous | 48.84 |
| Potassium chloride | 311.8 |
| Sodium chloride | 6999.5 |
| Sodium phosphate dibasic anhydrous | 71.02 |
| Sodium phosphate monobasic monohydrate | 62.5 |
| Zinc sulfate heptahydrate | 0.4315 |

The medium for inoculum culture (as opposed for the production phase) was usually supplemented with 5 mM glutamine, 8 g/L glucose, and 75-2000 nM Methotroxate.

For studies pH adjustment was performed as needed to maintain pH value at 7.00±0.10 using 1M Sodium Carbonate.

Adjustment in pH value was made in by adding 1 mL/L of 1M Sodium Carbonate to raise pH units up 0.10.

Cell culture was analyzed up to 14-days by taking a 3.5-mL sample and analyzed for viable cell count, viability, and cell size using a Beckman Coulter ViCell™-1.0 cell counter. Nutrient analysis was performed using the Nova 400 Biomedical Bioprofile®. Osmolality was measured using an Advanced® Instrument multi-sample Osmometer (Model 3900). Recombinant product titer concentration was obtained using the Agilent 1100 Series HPLC.

Recombinant Proteins.

The recombinant proteins produced were Apomab (TRAIL), anti-VEGF, and the immunoadhesin BR3-Fc.

Data Analysis.

Statistical analyses of the data were carried out using a full factorial design of experiment, which is an experiment whose design consists of two or more factors, each with discrete possible values or "levels", and whose experimental units take on all possible combinations of these levels across all such factors. A full factorial design may also be called a fully-crossed design. Such an experiment allows studying the effect of each factor on the response variable, as well as the effects of interactions between factors on the response variable.

Results

Figure 2:
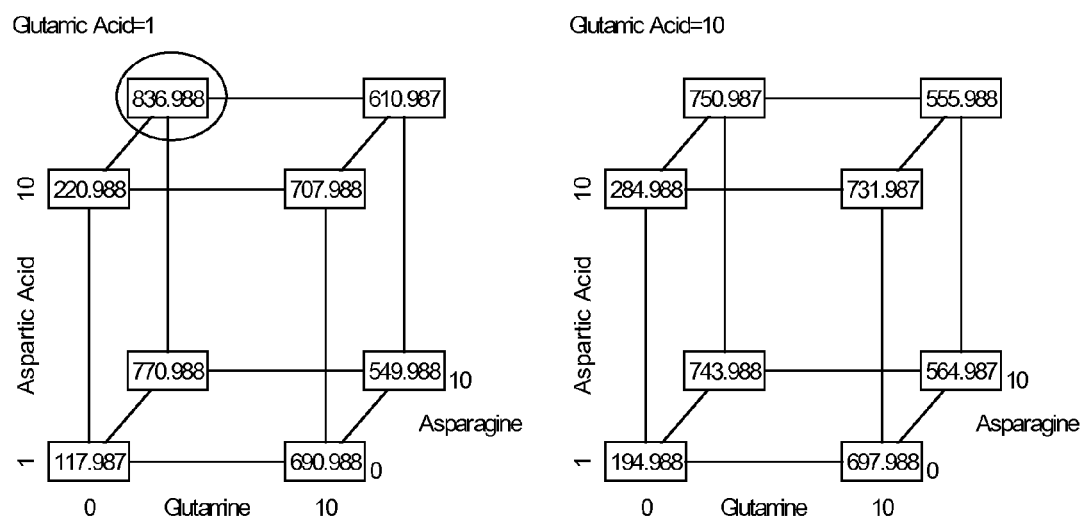
FIG. 2. BR3-Fc immunoadhesin cube plot analysis of titer results from a Full Factorial DOE evaluating the effect of different concentrations of Glutamine, Glutamate, Asparagine and Aspartate. The model predicts that the highest titer is achieved in Glutamine-Free media supplemented with 10 mM Asparagine, 10 mM Aspartic Acid and 1 mM Glutamic Acid.
Figure 3:
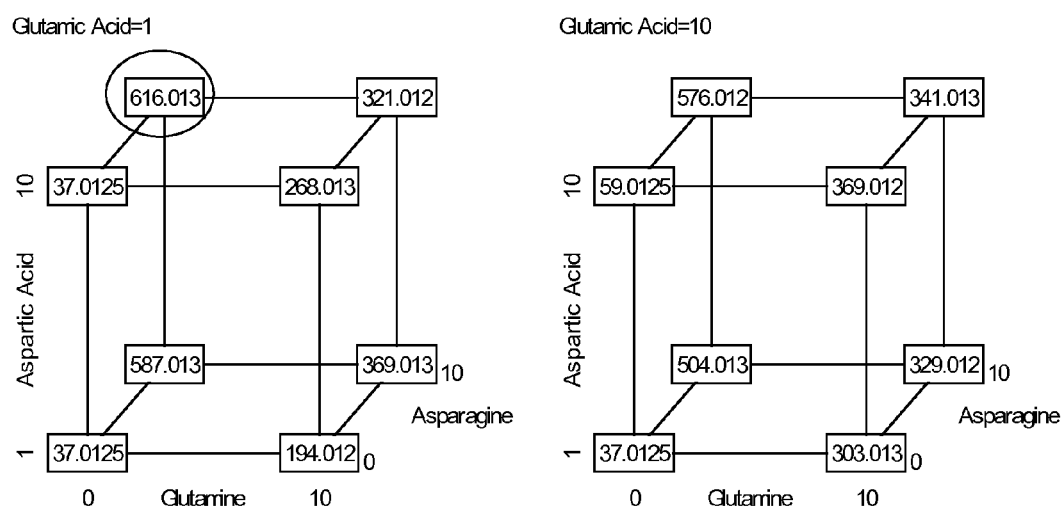
FIG. 3. anti-VEGF antibody cube plot analysis of titer results from a Full Factorial DOE evaluating the effect of different concentrations of Glutamine, Glutamate, Asparagine and Aspartate. The model predicts that the highest titer is achieved in Glutamine-Free media supplemented with 10 mM Asparagine, 10 mM Aspartic Acid and 1 mM Glutamic Acid.

As shown in FIGS. 1-5, use of a glutamine-free production medium increased the final recombinant protein titer of Apomab antibody, BR3-Fc immunoadhesin and anti-VEGF antibody. In each case, cube plot analysis of titer results using Full Factorial DOE evaluating the effect of different concentrations of Glutamine, Glutamate, Asparagine and Aspartate predict that the highest titer is achieved in Glutamine-Free media supplemented with 10 mM Asparagine, 10 mM Aspartic Acid and 1 mM Glutamic Acid. (FIGS. 1-3)

Figure 4:
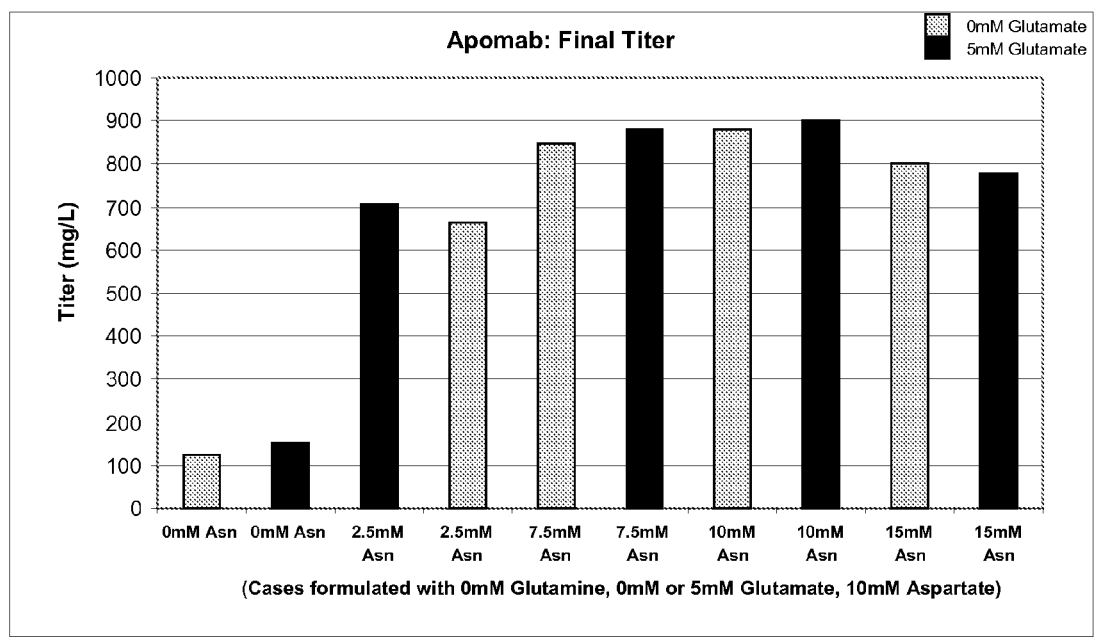
FIG. 4. Effect of Asparagine under Glutamine-free, low Glutamate and high Aspartate conditions on Apomab antibody titer. In Glutamine-free medium, Apomab antibody titer was significantly increased in the presence of 2.5-15 mM Asparagine compared to Glutamine-free cultures without Asparagine. Under these conditions, the presence or absence of Glutamate had no effect on titer.

The effect of Asparagine under Glutamine-free, low Glutamate and high Aspartate conditions on Apomab antibody titer is shown in FIG. 4. In Glutamine-free medium, Apomab antibody titer was significantly increased in the presence of 2.5-15 mM Asparagine compared to Glutamine-free cultures without Asparagine. Under these conditions, the presence or absence of Glutamate had no effect on titer.

Apomab antibody titer production across various Asparagine and Aspartate concentrations in Glutamine-free and low Glutamate conditions is illustrated in FIG. 5. A positive titration effect was observed when increasing Aspartate from 0 to 10 mM under these conditions.

Figure 6A:
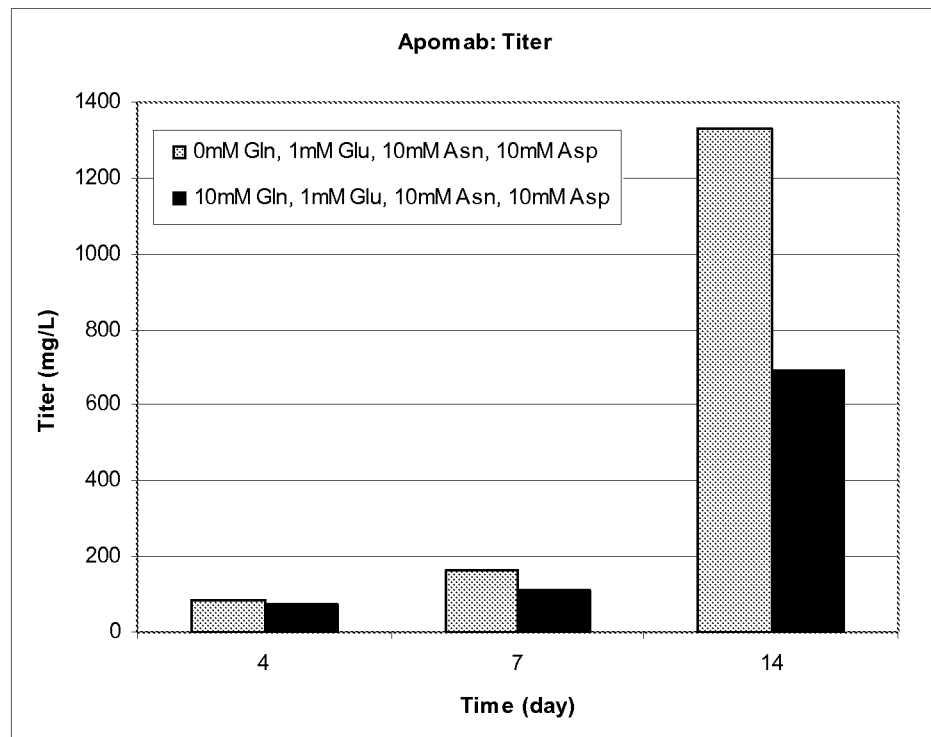
FIGS. 6. A-C. Effect of glutamine-free medium supplemented with 10 mM Asparagine, 10 mM Aspartic Acid and 1 mM Glutamic Acid on titer. The final titer for Apomab antibody, anti-VEGF antibody and BR3-Fc immunoadhesin was significantly higher in Glutamine-free medium compared to Glutamine-containing medium.
Figure 6B:
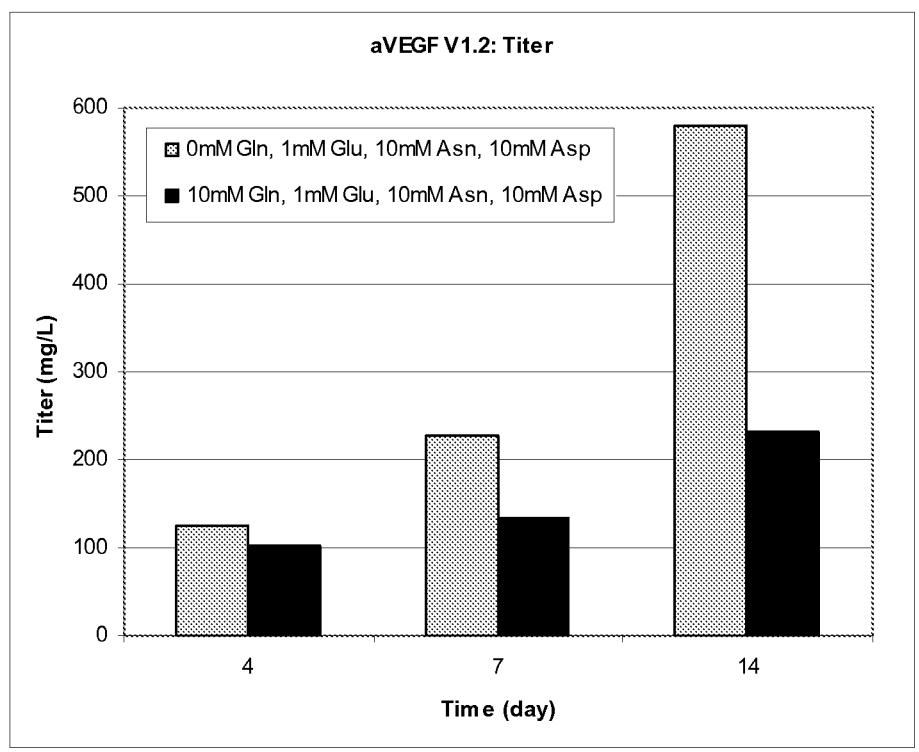
Figure 6C:
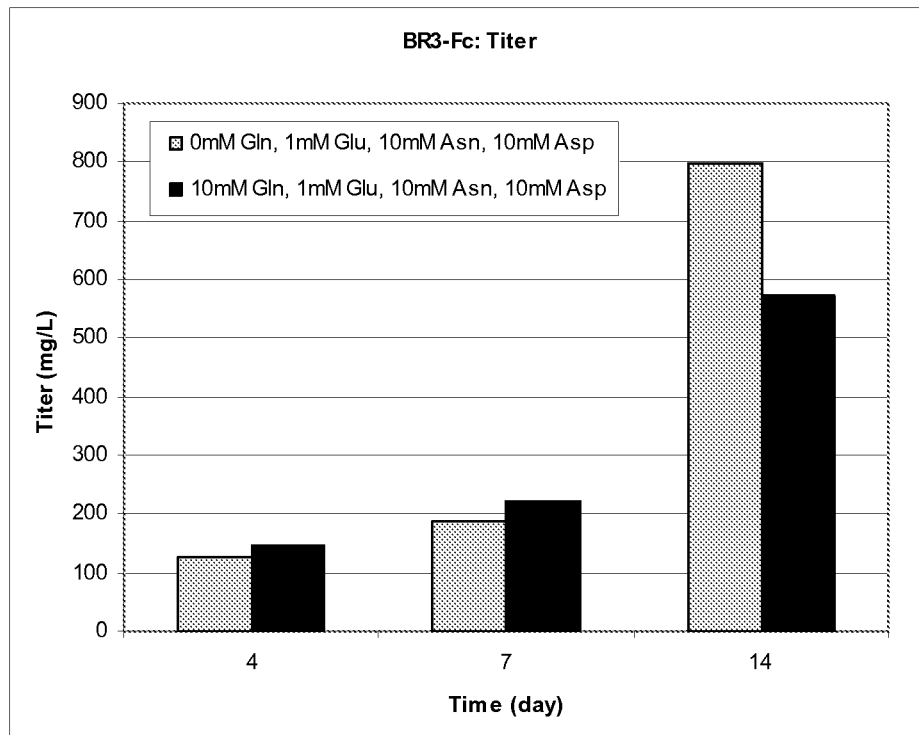

The effect of glutamine-free medium supplemented with 10 mM Asparagine, 10 mM Aspartic Acid and 1 mM Glutamic Acid on titer is demonstrated in FIGS. 6A-C, wherein the final titer for Apomab antibody, anti-VEGF antibody and BR3-Fc immunoadhesin (A-C, respectively) was significantly higher in Glutamine-free medium compared to Glutamine-containing medium.

Figure 7A:
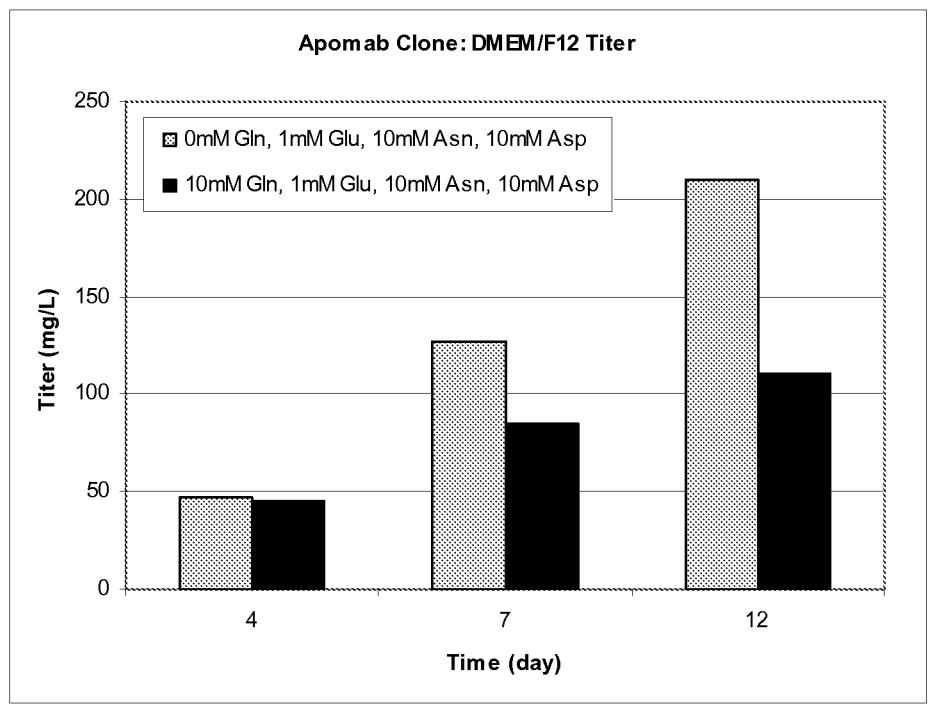
FIGS. 7A and B. Effect of DMEM/F12 glutamine-free medium supplemented with 10 mM Asparagine, 10 mM Aspartic Acid and 1 mM Glutamic Acid on titer. The final titer for Apomab antibody and anti-VEGF antibody was significantly higher in Glutamine-free DMEM/F12 medium compared to Glutamine-containing DMEM F12 medium.
Figure 7B:
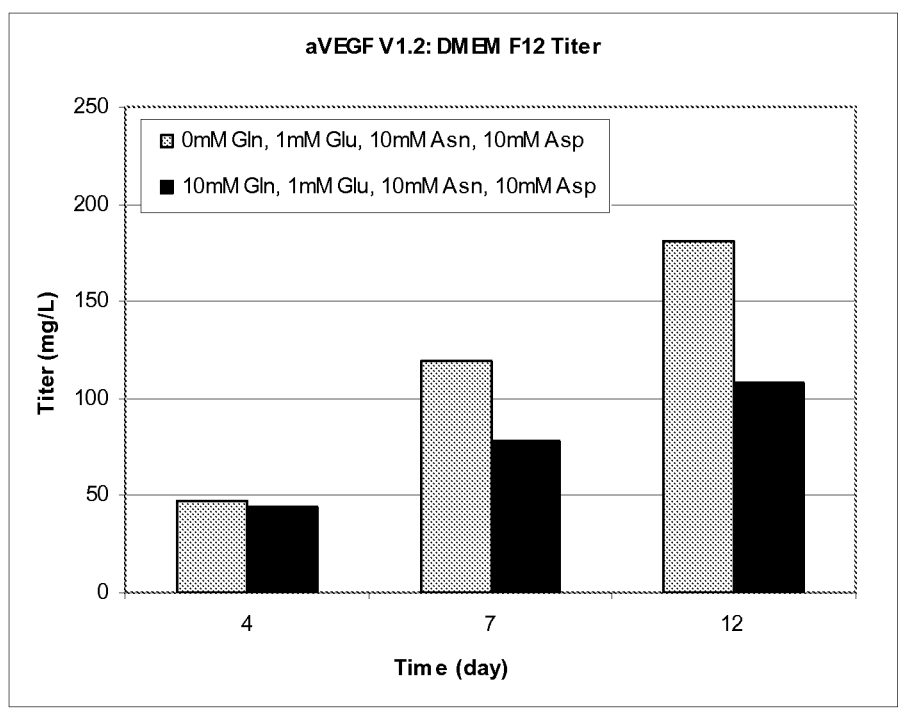

Similar results were obtained using the commercial DMEM/F-12 culture medium. As shown in FIGS. 7A and B, the final titer for Apomab antibody and anti-VEGF antibody (A and B, respectively) was significantly higher in Glutamine-free DMEM/F12 medium supplemented with 10 mM Asparagine, 10 mM Aspartic Acid and 1 mM Glutamic Acid compared to Glutamine-containing DMEM F12 medium supplemented with 10 mM Asparagine, 10 mM Aspartic Acid and 1 mM Glutamic Acid.

Figure 8A:
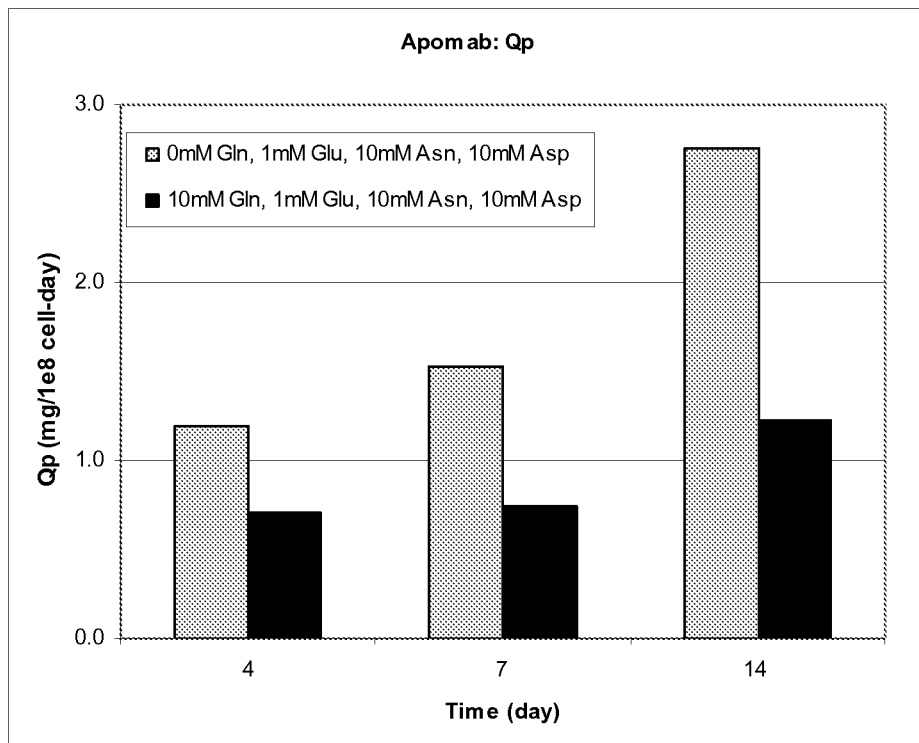
FIGS. 8A-C. Effect of glutamine-free medium supplemented with 10 mM Asparagine, 10 mM Aspartic Acid and 1 mM Glutamic Acid on cell specific productivity (Qp). Cell specific productivity for Apomab antibody, anti-VEGF antibody and BR3-Fc immunoadhesin was significantly higher in Glutamine-free medium compared to Glutamine-containing medium.
Figure 8B:
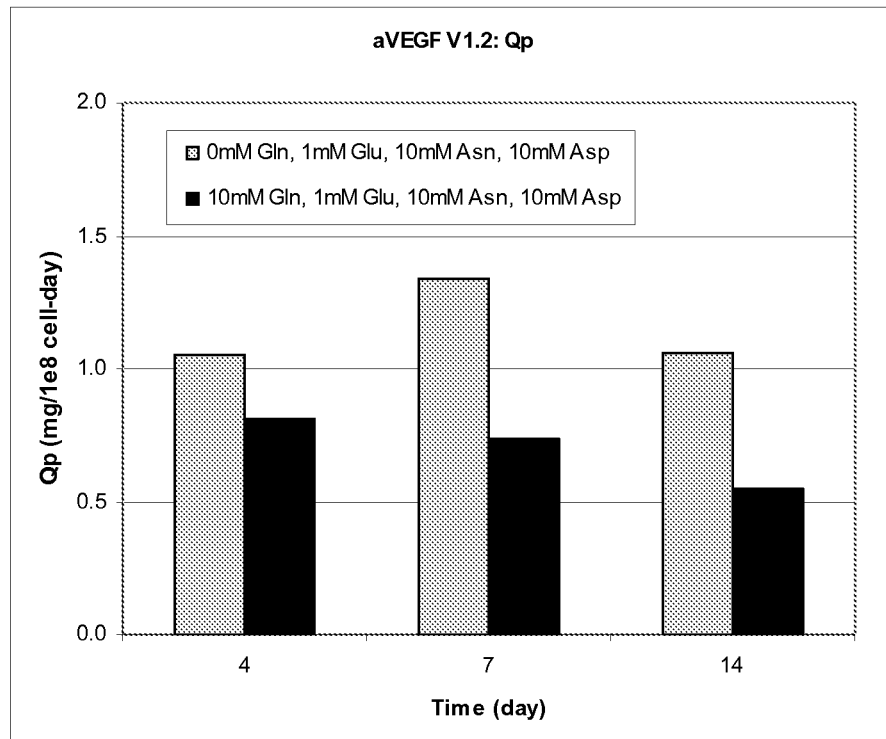
Figure 8C:
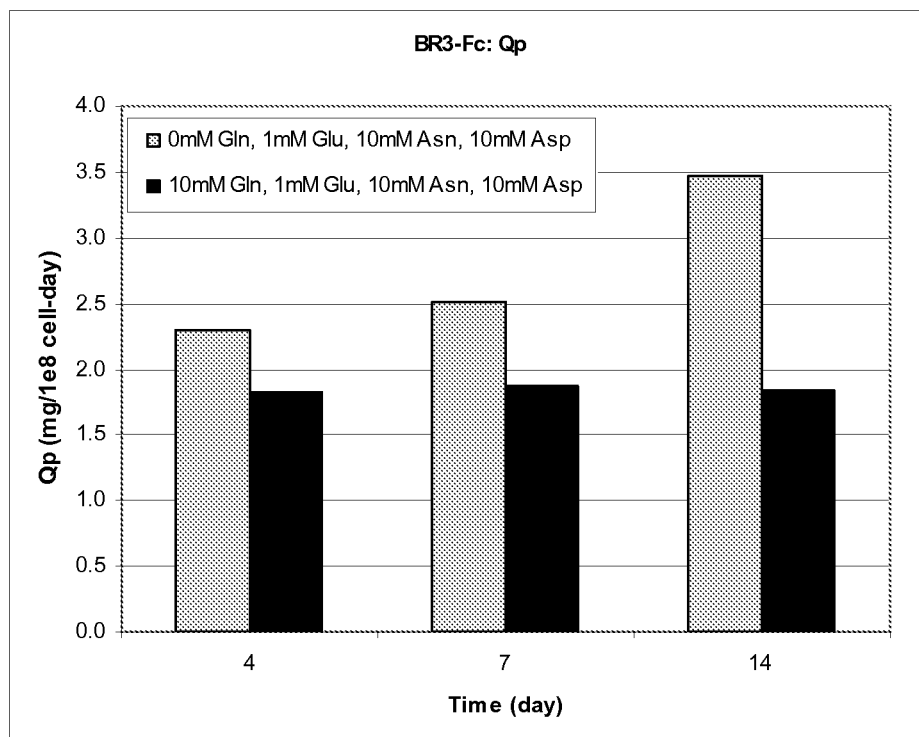
Figure 9A:
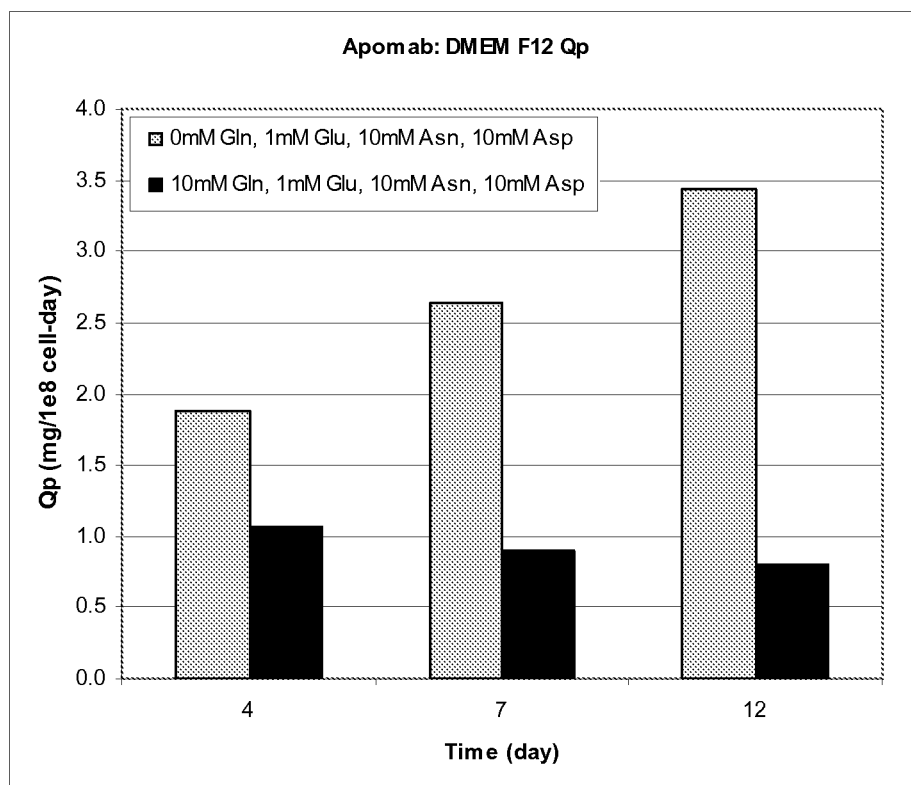
FIGS. 9A and B. Effect of DMEM/F12 glutamine-free medium supplemented with 10 mM Asparagine, 10 mM Aspartic Acid and 1 mM Glutamic Acid on cell specific productivity (Qp). Cell specific productivity for Apomab antibody and anti-VEGF antibody was significantly higher in Glutamine-free DMEM/F12 medium compared to Glutamine-containing DMEM/F12 medium.
Figure 9B:
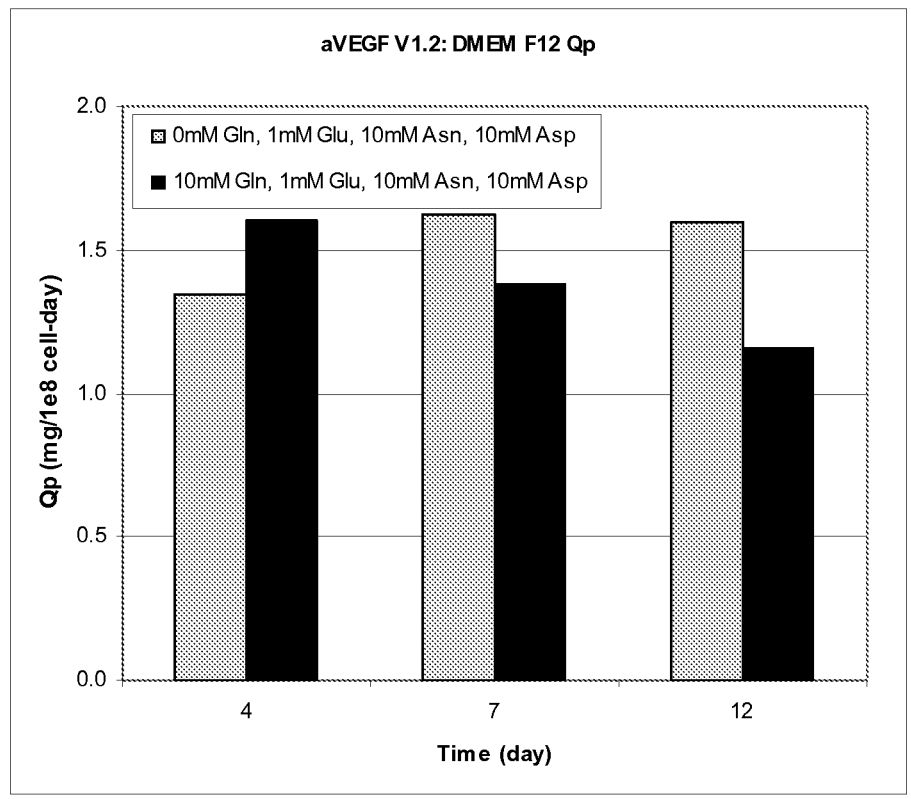

As shown in FIGS. 8 and 9, use of a glutamine-free production medium also increased specific production measured as Qp (mg/mL-cell/day). FIGS. 8 A-C illustrate that cell specific productivity (Qp) for Apomab antibody, anti-VEGF antibody and BR3-Fc immunoadhesin (A-C, respectively) was significantly higher in Glutamine-free medium supplemented with 10 mM Asparagine, 10 mM Aspartic Acid and 1 mM Glutamic Acid compared to Glutamine-containing medium. FIGS. 9A and B illustrate that cell specific productivity for Apomab antibody and anti-VEGF antibody (A and B, respectively) was significantly higher in Glutamine-free DMEM/F12 medium supplemented with 10 mM Asparagine, 10 mM Aspartic Acid and 1 mM Glutamic Acid compared to Glutamine-containing DMEM/F12 medium.

Figure 10A:
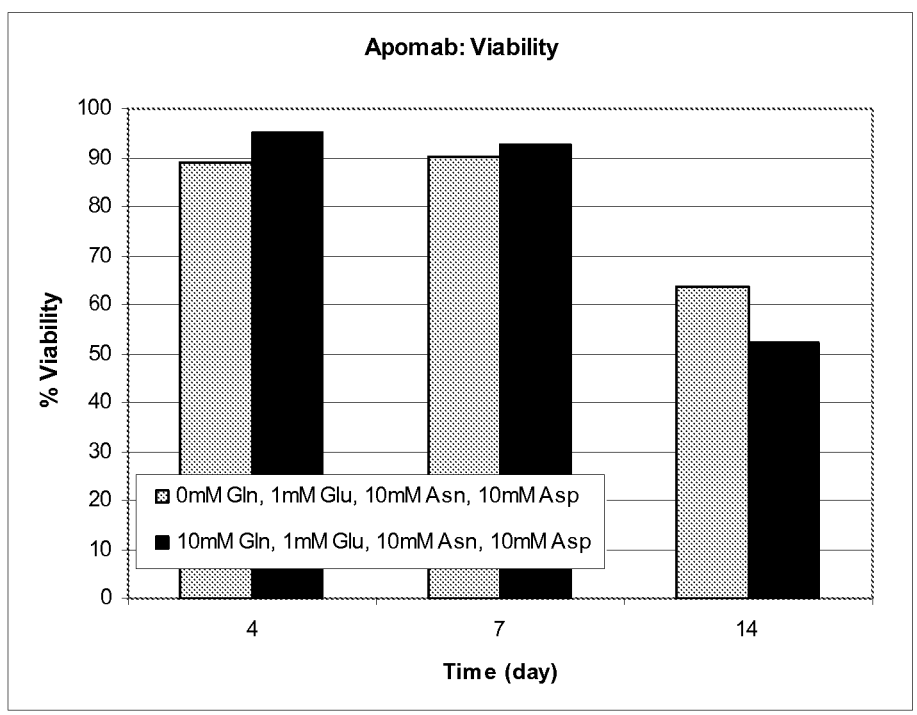
FIGS. 10A-C. Effect of glutamine-free medium supplemented with 10 mM Asparagine, 10 mM Aspartic Acid and 1 mM Glutamic Acid on Cell Viability. Cell viability for Apomab antibody, anti-VEGF antibody and BR3-Fc immunoadhesin was higher in Glutamine-free medium compared to Glutamine-containing medium.
Figure 10B:
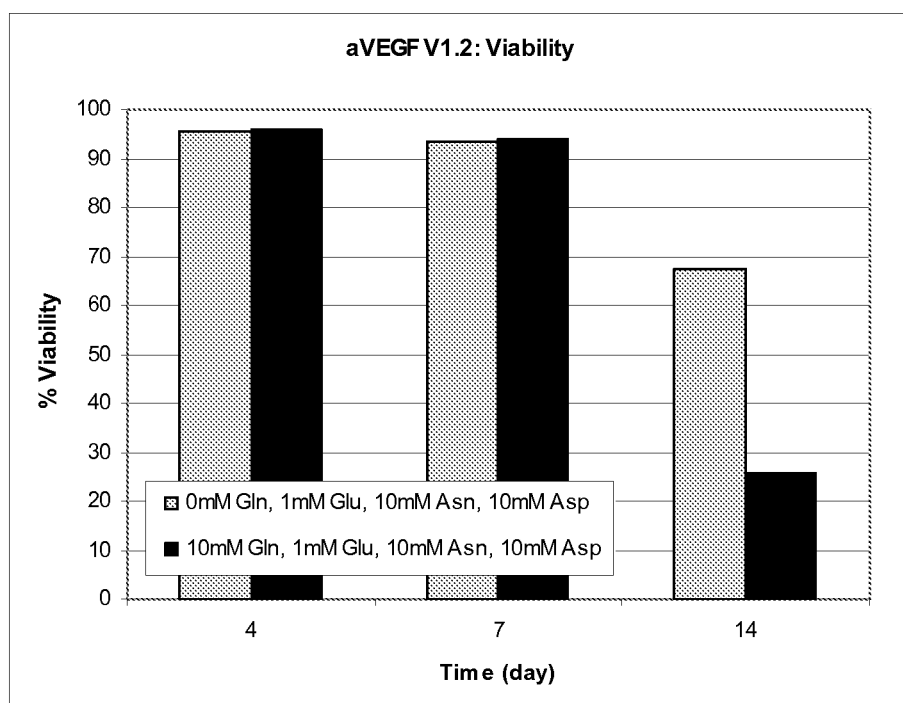
Figure 10C:
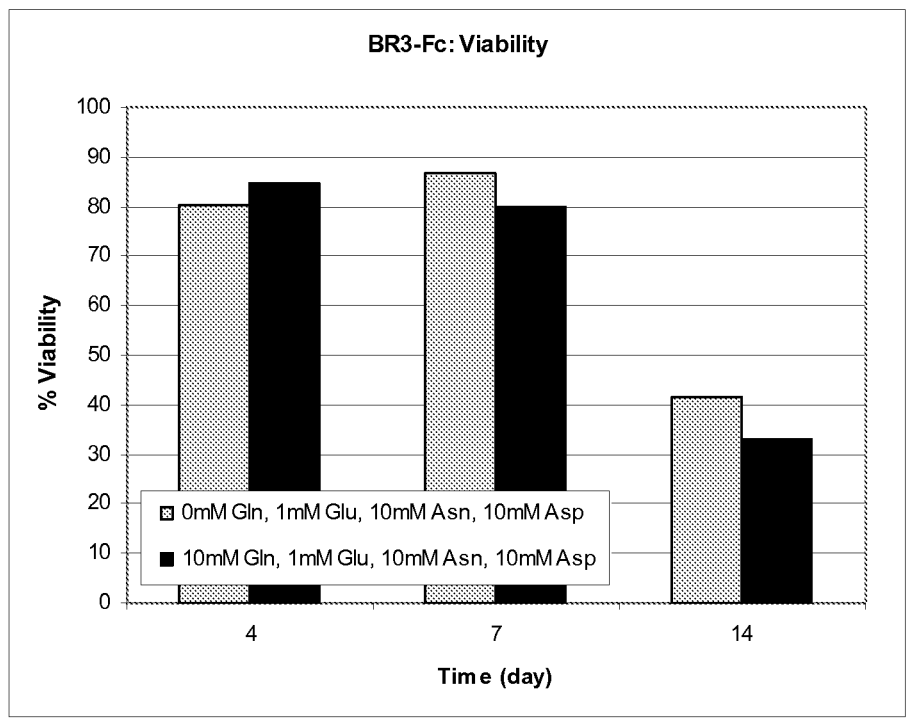
Figure 11A:
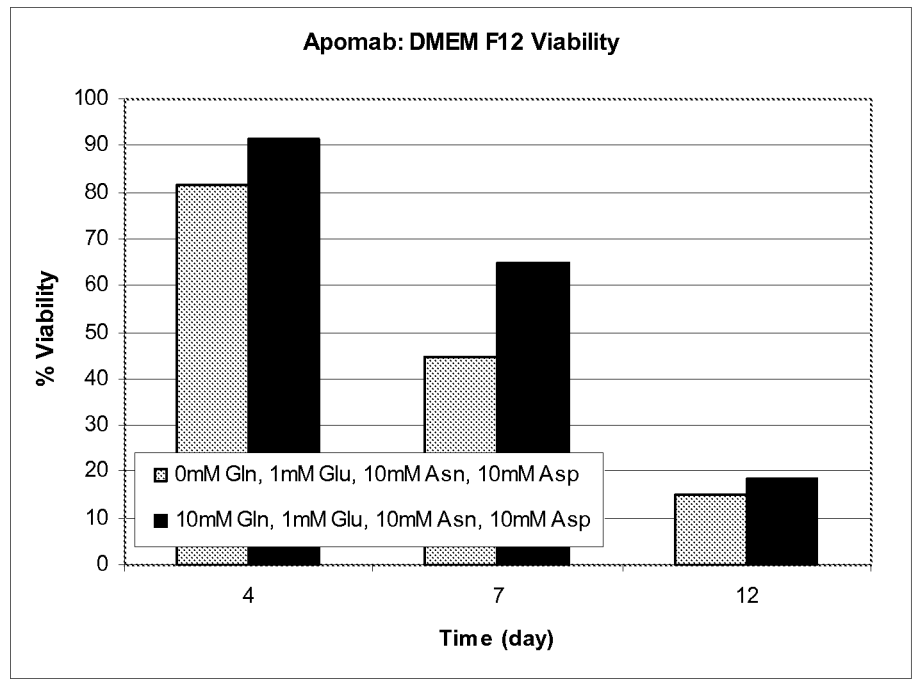
FIGS. 11A and B. Effect of DMEM/F12 glutamine-free medium supplemented with 10 mM Asparagine, 10 mM Aspartic Acid and 1 mM Glutamic Acid on Cell Viability. In DMEM/F12 medium, cell viability was not consistently improved in Glutamine-free medium. Viability was higher for Apomab antibody, but lower for anti-VEGF antibody compared to Glutamine containing medium.
Figure 11B:
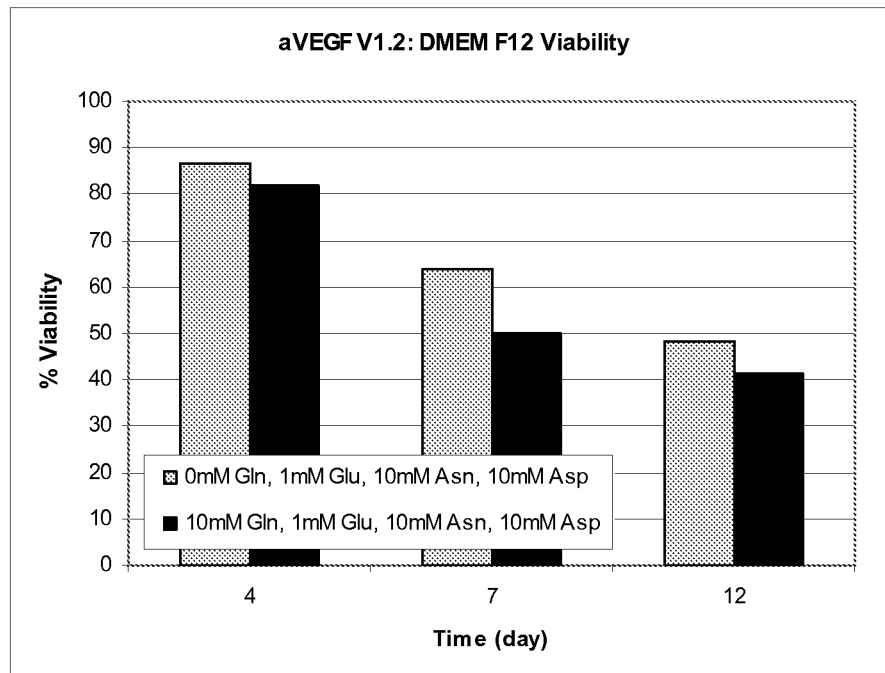

As shown in FIGS. 10 and 11, use of a glutamine-free production medium was shown to improve cell viability and extend culture longevity significantly. FIGS. 10A-C. illustrate that cell viability for Apomab antibody, anti-VEGF antibody and BR3-Fc immunoadhesin (A-C, respectively) was higher in Glutamine-free medium supplemented with 10 mM Asparagine, 10 mM Aspartic Acid and 1 mM Glutamic Acid compared to Glutamine-containing medium. FIGS. 11A and B indicate that, in DMEM/F12 medium, cell viability was not consistently improved in Glutamine-free medium supplemented with 10 mM Asparagine, 10 mM Aspartic Acid and 1 mM Glutamic Acid. Of note, viability was higher for Apomab antibody (FIG. 11A), but lower for anti-VEGF antibody (FIG. 11B) compared to Glutamine containing medium.

Figure 12A:
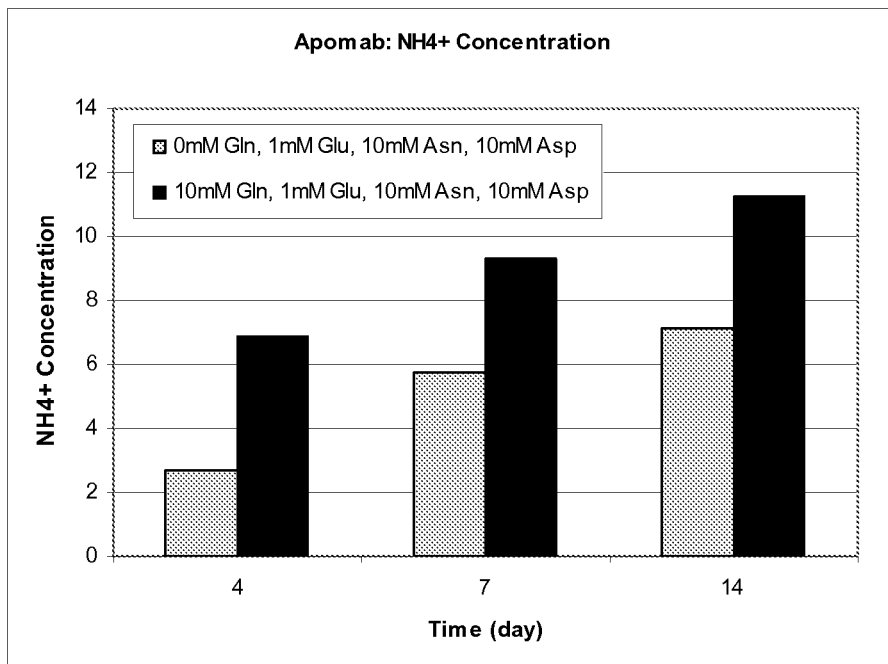
FIGS. 12 A-C. Effect of glutamine-free medium supplemented with 10 mM Asparagine, 10 mM Aspartic Acid and 1 mM Glutamic Acid on ammonia formation Ammonia was usually lower in Glutamine-free cultures compared to Glutamine-containing cultures.
Figure 12B:
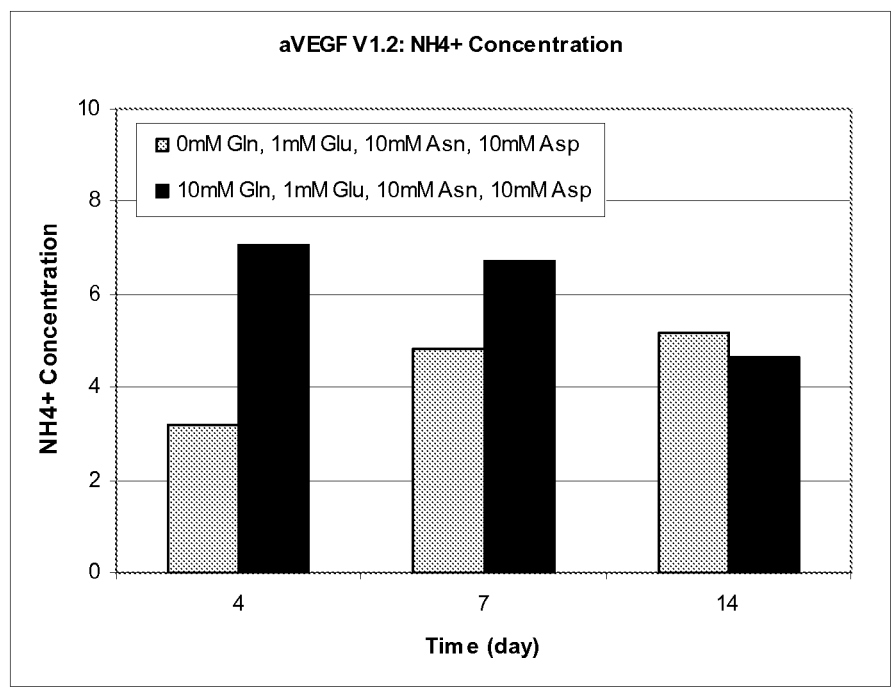
Figure 12C:
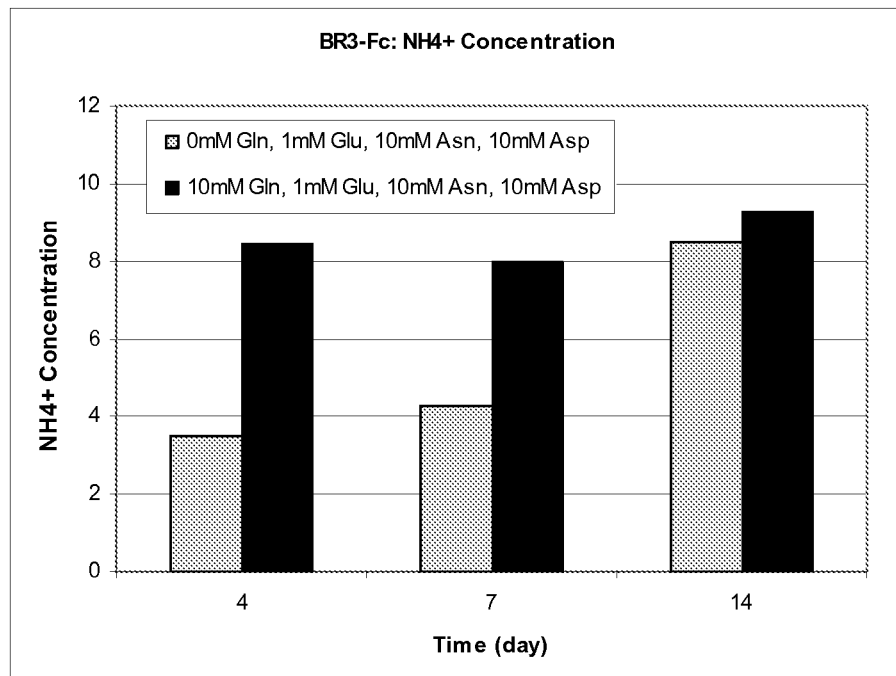
Figure 13A:
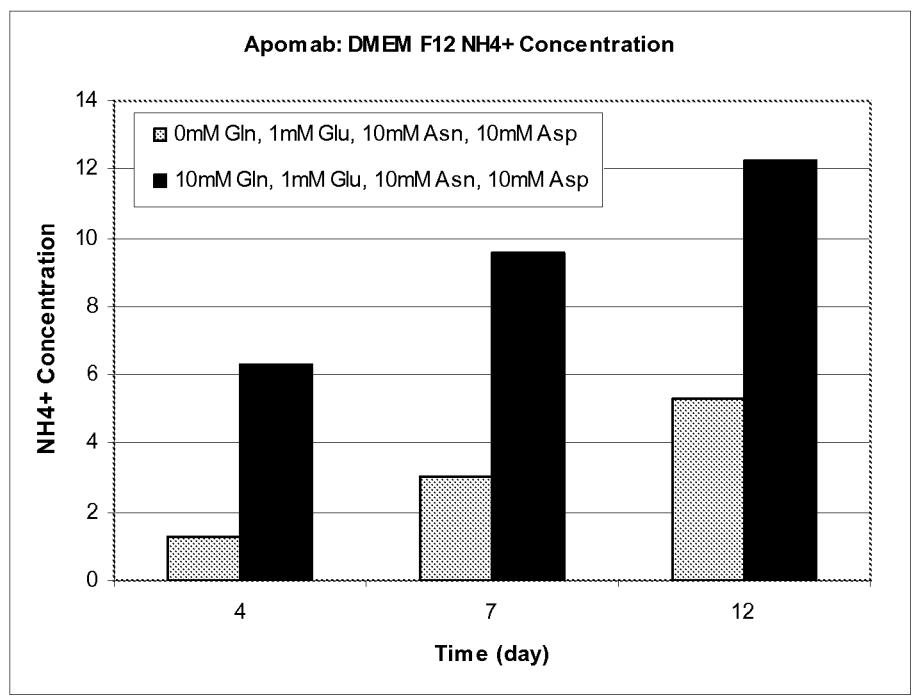
FIGS. 13A and B. Effect of DMEM/F12 glutamine-free medium supplemented with 10 mM Asparagine, 10 mM Aspartic Acid and 1 mM Glutamic Acid on ammonia formation. Ammonia was significantly reduces in Glutamine-free DMEM/F12 medium compared to Glutamine-containing DMEM/F12 medium.
Figure 13B:
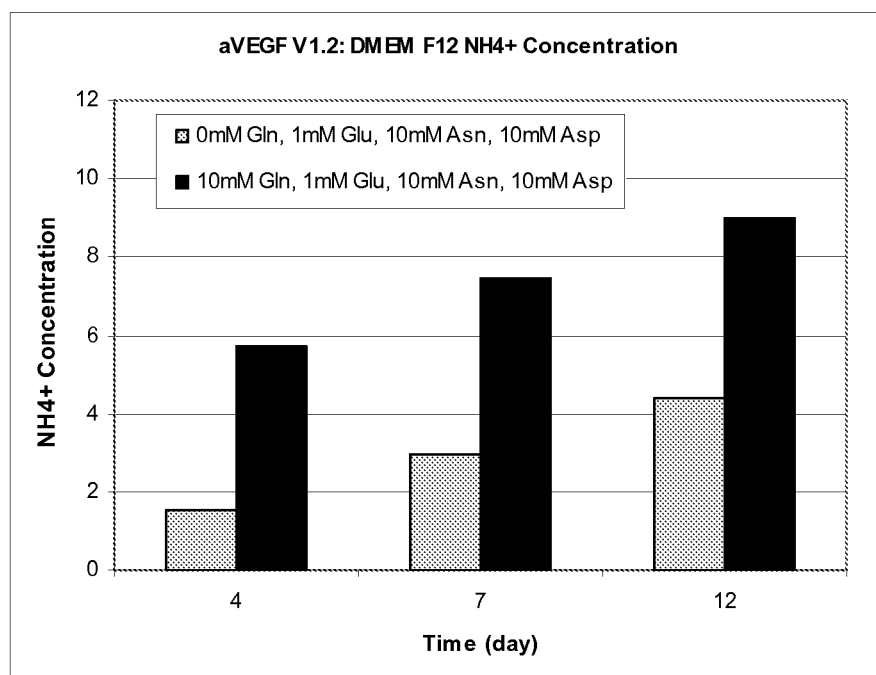

As shown in FIGS. 12 and 13, use of a glutamine-free production medium reduced $NH_4^+$ accumulation significantly compared to glutamine-containing medium. FIGS. 12 A-C illustrate that ammonia levels were usually lower in Glutamine-free cultures supplemented with 10 mM Asparagine, 10 mM Aspartic Acid and 1 mM Glutamic Acid compared to Glutamine-containing cultures. FIGS. 13 A and B illustrate that ammonia levels were significantly reduced in Glutamine-free DMEM/F12 medium supplemented with 10 mM Asparagine, 10 mM Aspartic Acid and 1 mM Glutamic Acid compared to Glutamine-containing DMEM/F12 medium.

The invention illustratively described herein can suitably be practiced in the absence of any element or elements, limitation or limitations that is not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalent of the invention shown or portion thereof, but it is recognized that various modifications are possible within the scope of the invention claimed. Thus, it should be understood that although the present invention has been specifically disclosed by preferred embodiments and optional features, modifications and variations of the inventions embodied herein disclosed can be readily made by those skilled in the art, and that such modifications and variations are considered to be within the scope of the inventions disclosed herein.

From the description of the invention herein, it is manifest that various equivalents can be used to implement the concepts of the present invention without departing from its scope. Moreover, while the invention has been described with specific reference to certain embodiments, a person of ordinary skill in the art would recognize that changes can be made in form and detail without departing from the spirit and the scope of the invention. The described embodiments are considered in all respects as illustrative and not restrictive. It should also be understood that the invention is not limited to the particular embodiments described herein, but is capable of many equivalents, rearrangements, modifications, and substitutions without departing from the scope of the invention.

What is claimed is:

1. A process for producing a polypeptide in a mammalian host cell expressing said polypeptide, comprising culturing the mammalian host cell in a production phase of the culture in a glutamine-free production culture medium containing asparagine, wherein the asparagine is added at a concentration in the range of 7.5 mM to 15 mM.

2. The process of claim 1 wherein the asparagine is added at a concentration in the range of 7.5 mM to 10 mM.

3. The process of claim 1 wherein said recombinant host cell is an eukaryotic host cell.

4. The process of claim 3 wherein said eukaryotic host cell is a Chinese Hamster Ovary (CHO) cell.

5. The process of claim 4 wherein the mammalian host cell is a dhfr⁻CHO cell.

6. The process of claim 1 wherein the production medium is serum-free.

7. The process of claim 1 wherein the production culture medium comprises one or more ingredients selected from the group consisting of
   1) an energy source;
   2) essential amino acids;
   3) vitamins;
   4) free fatty acids; and
   5) trace elements.

8. The process of claim 7 wherein the production culture medium additionally comprises one or more ingredients selected from the group consisting of:
   1) hormones and other growth factors;
   2) salts and buffers; and
   3) nucleosides.

9. The process of claim 1 wherein the production phase is a batch or fed batch culture phase.

10. The process of claim 1 further comprising the step of isolating said polypeptide.

11. The process of claim 10 further comprising determining one or more of cell viability, culture longevity, specific productivity and final recombinant protein titer following isolation.

12. The process of claim 11 wherein at least one of the cell viability, culture longevity, specific productivity and final recombinant protein titer is increased relative to the same polypeptide produced in a glutamine-containing production medium of the same composition.

13. The process of claim 1 wherein the polypeptide is a mammalian glycoprotein.

14. The process of claim 1 wherein the polypeptide is selected from the group consisting of antibodies, antibody fragments, and immunoadhesins.

15. The process of claim 14 wherein said antibody fragment is selected from the group consisting of Fab, Fab', F(ab')2, scFv, (scFv)2, dAb, complementarity determining region (CDR) fragments, linear antibodies, single-chain antibody molecules, minibodies, diabodies, and multispecific antibodies formed from antibody fragments.

16. The process of claim 14 wherein the antibody or antibody fragment is chimeric, humanized or human.

17. The process of claim 14 wherein said antibody or antibody fragment is a therapeutic antibody or a biologically functional fragment thereof.

18. The process of claim 17 wherein said therapeutic antibody is selected from the group consisting of anti-HER2 antibodies anti-CD20 antibodies; anti-IL-8 antibodies; anti-VEGF antibodies; anti-CD40 antibodies, anti-CD11a antibodies; anti-CD18 antibodies; anti-IgE antibodies; anti-Apo-2 receptor antibodies; anti-Tissue Factor (TF) antibodies; anti-human α4β7 integrin antibodies; anti-EGFR antibodies; anti-CD3 antibodies; anti-CD25 antibodies; anti-CD4 antibodies; anti-CD52 antibodies; anti-Fc receptor antibodies; anti-carcinoembryonic antigen (CEA) antibodies; antibodies directed against breast epithelial cells; antibodies that bind to colon carcinoma cells; anti-CD38 antibodies; anti-CD33 antibodies; anti-CD22 antibodies; anti-EpCAM antibodies; anti-GpIIb/IIIa antibodies; anti-RSV antibodies; anti-CMV antibodies; anti-HIV antibodies; anti-hepatitis antibodies; anti-CA 125 antibodies; anti-αvβ3 antibodies; anti-human renal cell carcinoma antibodies; anti-human 17-1A antibodies; anti-human colorectal tumor antibodies; anti-human melanoma antibody R24 directed against GD3 ganglioside; anti-human squamous-cell carcinoma; and anti-human leukocyte antigen (HLA) antibodies, and anti-HLA DR antibodies.

19. The process of claim 17 wherein said therapeutic antibody is an antibody binding to a HER receptor, VEGF, IgE, CD20, CD11a, CD40, BR3 or DR5.

20. The process of claim 19 wherein said therapeutic antibody binding to DR5 is selected from the group consisting of Apomabs 1.1, 2.1, 3.1, 4.1, 5.1, 5.2, 5.3, 6.1, 6.2, 6.3, 7.1, 7.2, 7.3, 8.1, 8.3, 9.1, 1.2, 2.2, 3.2, 4.2, 5.2, 6.2, 7.2, 8.2, 9.2, 1.3, 2.2, 3.3, 4.3, 5.3, 6.3, 7.3, 8.3, 9.3, and 25.3.

21. The process of claim 19 wherein said therapeutic antibody is an anti-BR3 antibody.

22. The process of claim 14 wherein said immunadhesin is a BR3-Fc immunoadhesin.

23. The process of claim 1 wherein said polypeptide is a therapeutic polypeptide.

24. The process of claim 23 wherein said therapeutic polypeptide is selected from the group consisting of a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\beta$5; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20, CD34, and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of said polypeptides.

25. A ready-to-use glutamine-free cell culture medium containing asparagine for the production of a polypeptide in a production phase, wherein the asparagine is at a concentration in the range of 7.5 mM to 15 mM.

* * * * *